US010041901B2

(12) United States Patent
Riggles et al.

(10) Patent No.: US 10,041,901 B2
(45) Date of Patent: Aug. 7, 2018

(54) ELECTRODE CONFIGURATION FOR A BIOSENSOR

(71) Applicant: Roche Diabetes Care, Inc., Indianapolis, IN (US)

(72) Inventors: Randall K. Riggles, Indianapolis, IN (US); Abner D. Joseph, Carmel, IN (US); Scott E. Carpenter, Pendleton, IN (US); Harvey E. Buck, Jr., Indianapolis, IN (US); Georgeta C. Lica, Indianapolis, IN (US); Terry A. Beaty, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 891 days.

(21) Appl. No.: 13/837,083

(22) Filed: Mar. 15, 2013

(65) Prior Publication Data
US 2014/0262773 A1 Sep. 18, 2014

(51) Int. Cl.
G01N 27/327 (2006.01)

(52) U.S. Cl.
CPC .................. *G01N 27/3272* (2013.01)

(58) Field of Classification Search
CPC .... G01N 27/327–27/3274; C12Q 1/00; C12Q 1/001; C12Q 1/004; C12Q 1/005; C12Q 1/006; C12Q 1/26; C12Q 1/34; C12Q 1/54

See application file for complete search history.

(56) References Cited

U.S. PATENT DOCUMENTS

| 5,989,409 A | 11/1999 | Kurnik et al. |
| 6,749,740 B2 | 6/2004 | Liamos et al. |
| RE38,681 E | 1/2005 | Kurnik et al. |

(Continued)

FOREIGN PATENT DOCUMENTS

| EP | 0924520 A | 6/1999 |
| EP | 1182451 | 2/2002 |

(Continued)

OTHER PUBLICATIONS

US 7,195,705, 03/2007, Wilsey (withdrawn)

*Primary Examiner* — Maris R Kessel
(74) *Attorney, Agent, or Firm* — Maschoff Brennan

(57) ABSTRACT

A biosensor including a capillary chamber having an inner boundary, a working electrode including an effective working electrode portion positioned within the capillary chamber, and a counter electrode including an effective counter electrode portion positioned within the capillary chamber, and with the working and counter electrodes each having a neck that constitutes the sole portion of the electrodes that extends across the inner boundary and out of the capillary chamber. In one embodiment, the effective working electrode portion defines an average working electrode width, and the working electrode neck defines a working electrode neck width that is reduced relative to the average working electrode width. In another embodiment, a ratio between the area of the effective working electrode portion exposed to the capillary chamber and the area of the effective counter electrode portion exposed to the capillary chamber is substantially constant as a position of the inner boundary of the capillary chamber is varied along a length of the working and counter electrode necks.

25 Claims, 8 Drawing Sheets

(56) References Cited

U.S. PATENT DOCUMENTS

| | | |
|---|---|---|
| 6,863,800 B2 | 3/2005 | Karinka et al. |
| 6,893,545 B2 | 5/2005 | Gotoh et al. |
| RE38,775 E | 8/2005 | Kurnik et al. |
| 7,073,246 B2 | 7/2006 | Bhullar et al. |
| 7,294,246 B2 | 11/2007 | Gundel et al. |
| 7,387,714 B2 | 6/2008 | Gundel et al. |
| 7,887,682 B2 | 2/2011 | Wang et al. |
| 7,955,492 B2 | 6/2011 | Fujiwara et al. |
| 2002/0179441 A1* | 12/2002 | Yamanishi ............ C12Q 1/006 204/403.01 |
| 2004/0194302 A1 | 10/2004 | Bhullar et al. |
| 2005/0098434 A1 | 5/2005 | Gundel et al. |
| 2009/0071847 A1 | 3/2009 | Edelbrock et al. |
| 2009/0240166 A1 | 9/2009 | Wang et al. |
| 2011/0092010 A1 | 4/2011 | VanDuren et al. |
| 2011/0186428 A1 | 8/2011 | Beaty et al. |
| 2011/0198223 A1 | 8/2011 | Fujiwara et al. |
| 2011/0203926 A1 | 8/2011 | Musho et al. |

FOREIGN PATENT DOCUMENTS

| | | |
|---|---|---|
| JP | 05-072172 | 3/1993 |
| JP | 1999183423 A | 7/1999 |
| JP | 11-304748 | 11/1999 |
| WO | WO 99/13099 | 3/1999 |

\* cited by examiner

ELECTRODE CONFIGURATION FOR A BIOSENSOR

BACKGROUND

Electrochemical biosensors are known in the art and have been used to determine the concentration of various analytes from biological samples, particularly from blood. Various configurations of electrochemical biosensors are described in U.S. Pat. Nos. 5,413,690; 5,762,780; 5,798,031; 5,997,8171; 7,073,246; 7,195,805 and 7,473,398 and U.S. Patent Application Publication No. 2005/0016844, the disclosures of which are each expressly incorporated herein by reference in their entirety.

As the number of patients suffering from diabetes and similar medical conditions increases, self-monitoring of blood glucose where the patient monitors his or her blood glucose level has become common practice. The purpose of monitoring the blood glucose level is to determine the blood glucose concentration level, and then to take the requisite corrective action based on whether the level is too high or too low in order to bring the level back within a normal or acceptable range. Failure to take corrective action can result in serious medical implications. Glucose monitoring is a fact of everyday life for millions of diabetic individuals. Additionally, failure to test blood glucose levels properly and on a regular basis can result in serious diabetes-related complications, including cardiovascular disease, kidney disease, nerve damage and/or blindness.

A number of biosensors utilize electrochemical analysis to determine the blood glucose level by measuring a current that corresponds to an analyte concentration. Such biosensors may utilize a capillary chamber having an electrode substrate providing a working electrode area located in the capillary chamber. The current response of the electrochemical cell is directly proportional to the working electrode area. However, variations in the working electrode area may result from the manufacture and assembly of the components of the biosensor that define the capillary chamber and the position/location of the working electrode. Variations in the working electrode area in the capillary chamber from one biosensor to another are undesirable since such variations introduces imprecision and/or inaccuracy in the measured analyte concentration, which may in turn result in an imprecise and/or inaccurate measurement of the blood glucose level.

Therefore, biosensor arrangements which minimize variations in the working electrode area associated with the manufacture of the biosensor are desirable. Additionally, maintaining a balanced ratio between the counter electrode area and the working electrode area in the capillary chamber is also desirable in order to increase the precision and/or accuracy of the biosensor.

SUMMARY

The present invention generally relates to a biosensor, and more specifically relates to an electrode configuration for a biosensor having a relatively constant/balanced ratio between the counter electrode area and the working electrode area, and having a relatively low variation in the working electrode area.

According to one form, a biosensor is provided which includes a capillary chamber having an inner boundary, a working electrode including an effective working electrode portion positioned within the capillary chamber, and a counter electrode including an effective counter electrode portion positioned within the capillary chamber. The effective working electrode portion defines an average working electrode width and has a working electrode neck defining a working electrode neck width that is reduced relative to the average working electrode width. The working electrode neck constitutes the sole portion of the working electrode that extends across the inner boundary and out of the capillary chamber. The effective counter electrode portion has a counter electrode neck that constitutes the sole portion of the counter electrode that extends across the inner boundary and out of the capillary chamber.

According to another form, a biosensor is provided which includes a capillary chamber having an inner boundary, a working electrode including an effective working electrode portion positioned within the capillary chamber, and a counter electrode including an effective counter electrode portion positioned within the capillary chamber. The effective working electrode portion has a main body and a working electrode neck extending therefrom, with the working electrode neck constituting the sole portion of the working electrode that extends across the inner boundary and out of the capillary chamber. The effective counter electrode portion has a main body and a counter electrode neck extending therefrom, with the main body of the effective counter electrode portion positioned generally adjacent the main body of the effective working electrode portion, and with the counter electrode neck constituting the sole portion of the counter electrode that extends across the inner boundary and out of the capillary chamber.

According to another form, a biosensor is provided which includes a capillary chamber having an inner boundary, a working electrode including an effective working electrode portion positioned within the capillary chamber, and a counter electrode including an effective counter electrode portion positioned within the capillary chamber. The effective working electrode portion defines an effective working electrode area exposed to the capillary chamber, with the effective working electrode portion having a working electrode neck that constitutes the sole portion of the working electrode that extends out of the capillary chamber. The effective counter electrode portion defines an effective counter electrode area exposed to the capillary chamber, with the effective counter electrode portion having a counter electrode neck that constitutes the sole portion of the counter electrode that extends out of the capillary chamber. The working electrode neck and the counter electrode neck each extend across a single inner side wall defining the inner boundary of the capillary chamber, and a ratio between the effective working electrode area and the effective counter electrode area is substantially constant as a position of the single inner side wall is varied along a length of the working electrode neck and the counter electrode neck.

Further aspects, embodiments, forms, features, benefits, objects, and advantages shall become apparent from the detailed description and figures provided herewith.

BRIEF DESCRIPTION OF THE DRAWING FIGURES

DETAILED DESCRIPTION OF THE ILLUSTRATED EMBODIMENTS

Figure 1:
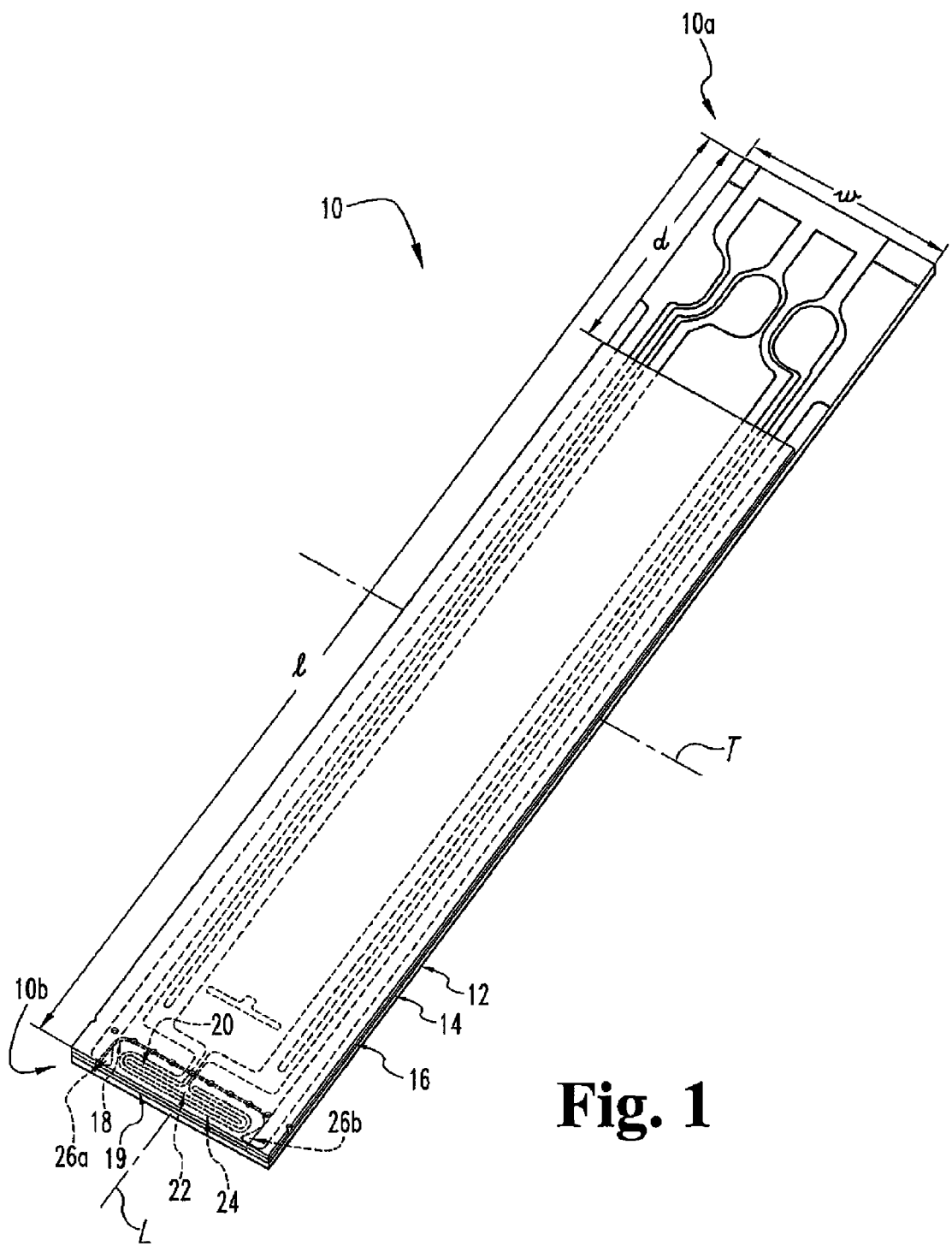
FIG. 1 is a perspective view of a biosensor according to one form of the present invention.

For purposes of promoting an understanding of the principles of the present invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated herein being contemplated as would normally occur to one skilled in the art to which the invention relates.

The present invention generally relates to a biosensor, and more specifically relates to an electrode configuration for a biosensor having a relatively constant/balanced ratio between the counter electrode area and the working electrode area, as well as a relatively low variation in the working electrode area, to thereby improve the precision and/or accuracy of current measurements in the electrochemical analysis of an analyte positioned in a capillary chamber of the biosensor. Aspects and features of the biosensor are presented in FIGS. 1-7 which are not necessarily drawn to scale and where like components in the various drawing figures are numbered alike.

Referring to FIGS. 1-6, shown therein are various aspects and features of a biosensor 10 according to one form of the present invention. In the illustrated embodiment, the biosensor 10 has a proximal end 10a and an opposite distal end 10b arranged along a longitudinal axis L, and generally includes an electrode support substrate 12, an intermediate spacer substrate 14 positioned on the support substrate 12, and a cover substrate or hydrophilic roof 16 positioned on the spacer substrate 14. The support substrate 12, the spacer substrate 14 and the cover substrate 16 cooperate with one another to define a capillary chamber or channel 18 having a sample inlet port 19 for receiving a fluid sample adjacent the distal end 10b of the biosensor 10. Additionally, the support substrate 12 includes an electrical conductor arrangement 20 including a series of electrodes 22, 24, 26a and 26b that each include one or more electrode portions positioned within the capillary chamber 18, further details of which will be set forth below. Although the illustrated embodiment of the biosensor 10 includes three separate substrates 12, 14 and 16 that are sandwiched together to form the capillary chamber 18, it should be understood that other embodiments are also contemplated including, for example, embodiments that do not include the cover substrate 16.

In the illustrated embodiment, the biosensor 10 is shown as having a rectangular configuration defining an overall length/extending generally along the longitudinal axis L between the proximal and distal ends 10a, 10b, and further defining an overall width w extending in a lateral direction generally along a transverse axis T. However, it should be understood that the biosensor 10 can be provided with other suitable shapes and configurations without departing from the principles of the present invention. It should be understood that the biosensor 10 can be any one of a substantial quantity of biosensors produced from rolls of material, sheets of material, or other material stock. In one embodiment, the selection of materials from which the biosensor 10 is constructed includes a stock sufficiently flexible for roll processing, but still rigid enough to provide a useful/sufficient stiffness to the biosensor 10. Additionally, the arrangement and configuration of the biosensor 10 and the manufacturing method associated with forming the biosensor 10 provides a relatively constant/balanced ratio between the counter electrode area and the working electrode area, as well as a relatively low variation in the working electrode area, to thereby improve the precision and/or accuracy of current measurements in the electrochemical analysis of an analyte positioned in the capillary chamber 18 of the biosensor 10, further details of which will be set forth below.

Referring collectively to FIGS. 4, 5a, 5b and 6, in the illustrated embodiment, the support substrate 12 has a rectangular configuration defining a length dimension substantially equal to the overall length/of the biosensor 10, and a width dimension substantially equal to the overall width w of the biosensor 10. The support substrate 12 includes a bottom/lower outer surface 30 defining an outer face of the biosensor 10, and a top/upper inner surface 32 facing a direction opposite the outer surface 30. Additionally, the support substrate 12 includes opposite first and second end surfaces or edges 34a, 34b extending generally along the transverse axis T (i.e., along the width dimension), and opposite first and second side surfaces or edges 36a, 36b extending generally along the longitudinal axis L (i.e., along the length dimension) between the end surfaces 34*a*, 34*b*. While the end surfaces 34*a*, 34*b* and the side surfaces 36*a*, 36*b* of the support substrate 12 are illustrated to form a generally rectangular shape, as indicated above, it should be understood that the biosensor 10, including the support substrate 12, may form other shapes and configurations without departing from the principles of the present invention. In one specific embodiment, the support substrate 12 is formed of a flexible polymer material including, for example, a polyester or polyimide such as polyethylene naphthalate (PEN). However, other suitable materials for the support substrate 12 are also contemplated.

As indicated above, the support substrate 12 includes an electrical conductor arrangement or ablated electrode pattern 20 including a series of electrodes 22, 24, 26*a* and 26*b*. The electrodes 22, 24, 26*a* and 26*b* are formed from an electrical conductor 28 extending along the inner surface 32 of the support substrate 12. Non-limiting examples of materials suitable for the electrical conductor 28 include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these or other elements. In one specific embodiment, the individual electrodes 22, 24, 26*a* and 26*b* are isolated from one another via laser ablation or laser scribing, and the electrodes 22, 24, 26*a* and 26*b* may be created by removing select portions of the electrical conductor 28 from an area extending around/along the electrodes 22, 24, 26*a* and 26*b* either broadly, such as by broad field ablation, or minimally, such as by line scribing. However, it should be understood that other suitable techniques for forming the electrodes 22, 24, 26*a* and 26*b* are also contemplated as would occur to those of ordinary skill in the art including, for example, lamination, screen-printing, or photolithography.

In the illustrated embodiment, the electrode 22 is configured as a working electrode, the electrode 24 is configured as a reference or counter electrode, and the electrodes 26*a*, 26*b* are configured as sample sufficiency electrodes, with at least a portion of each of the electrodes 22, 24, 26*a* and 26*b* positioned within and exposed to the capillary chamber 18. Further aspects regarding the configuration and arrangement of the electrodes 22, 24, 26*a* and 26*b* will be set forth in greater detail below. However, it should be understood that other suitable electrode configurations and arrangements are also contemplated as falling within the scope of the present invention.

Figure 4:
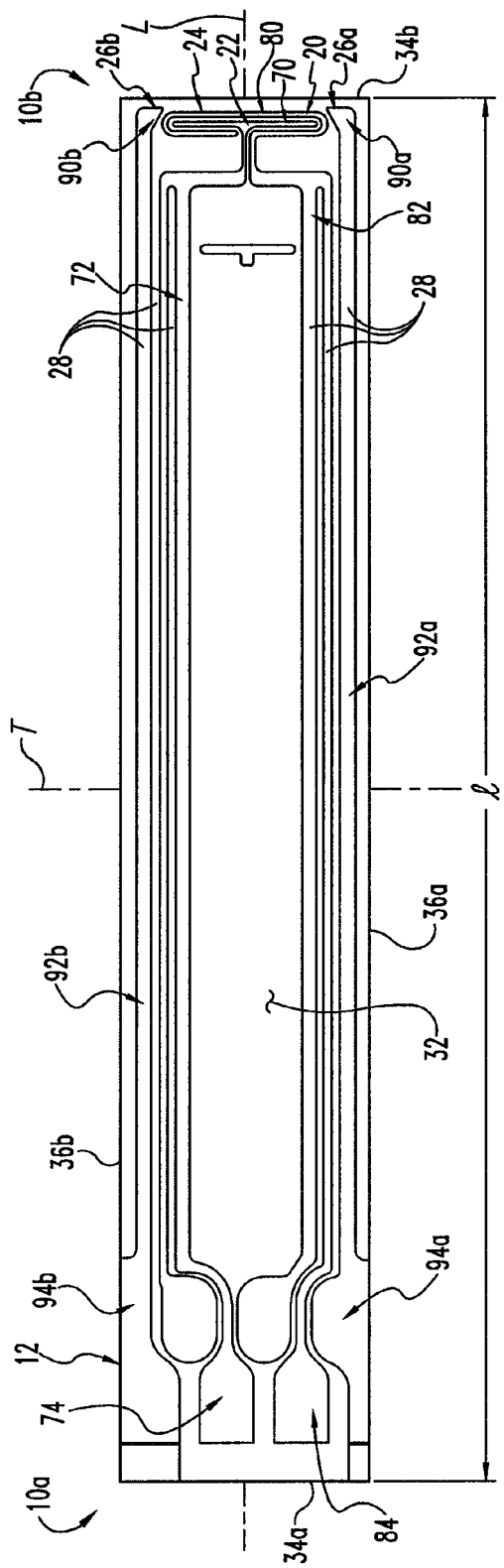
FIG. 4 is a top plan view of the biosensor of FIG. 3 with the spacer substrate removed.
Figure 6:
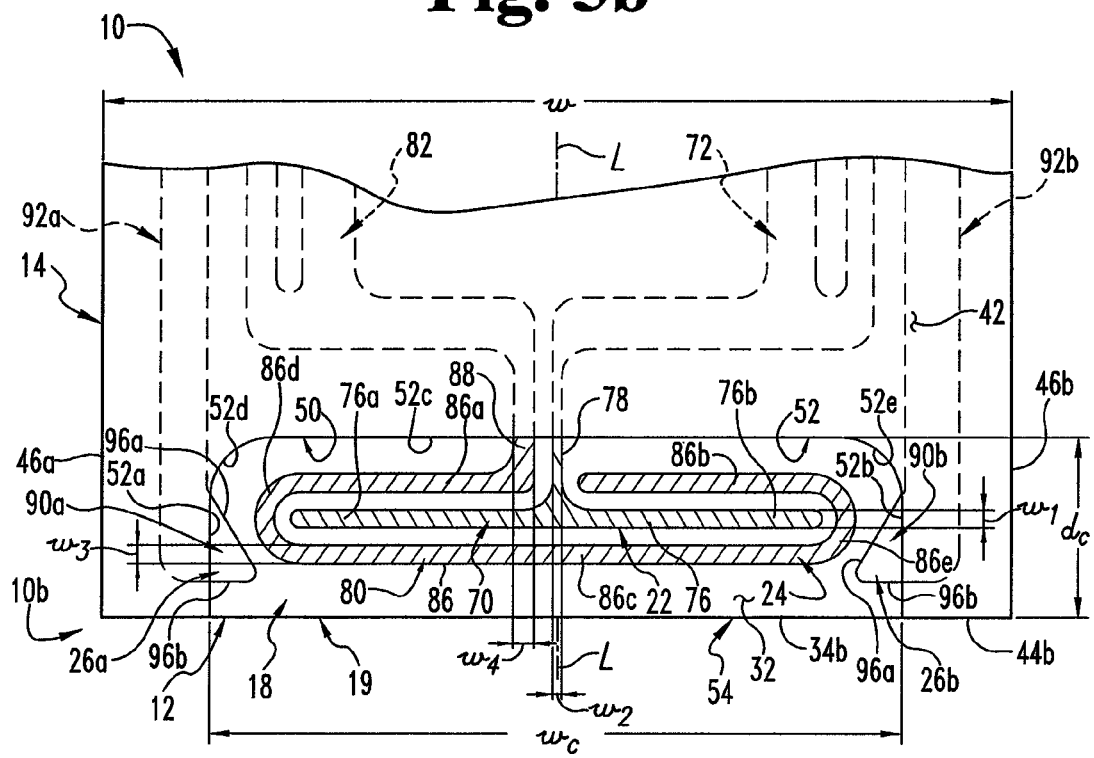
FIG. 6 is an enlarged plan view of the distal end portion of the biosensor of FIG. 1 illustrating the capillary chamber and the electrode configuration positioned therein.

Referring specifically to FIGS. 4 and 6, the working electrode 22 includes an effective working electrode portion 70 positioned within and exposed to the capillary chamber 18, at least one lead portion 72 extending away from the effective working electrode portion 70 and positioned outside of the capillary chamber 18, and at least one contact portion 74 extending from the lead portion 72 and positioned near the proximal end 10*a* of the biosensor 10. The counter electrode 24 includes an effective counter electrode portion 80 positioned within and exposed to the capillary chamber 18, at least one lead portion 82 extending from the effective counter electrode portion 80 and positioned outside of the capillary chamber 18, and at least one contact portion 84 extending from the lead portion 82 and positioned near the proximal end 10*a* of the biosensor 10. Additionally, the sample sufficiency electrodes 26*a* includes an effective sample sufficiency electrode portion 90*a* positioned within and exposed to the capillary chamber 18, a lead portion 92*a* extending from the effective sample sufficiency electrode portion 90*a* and positioned outside of the capillary chamber 18, and a contact portion 94*a* extending from the lead portion 92*a* and positioned near the proximal end 10*a* of the biosensor 10, and the sample sufficiency electrodes 26*b* similarly includes an effective sample sufficiency electrode portion 90*b* positioned within and exposed to the capillary chamber 18, a lead portion 92*b* extending from the effective sample sufficiency electrode portion 90*b* and positioned outside of the capillary chamber 18, and a contact portion 94*b* extending from the lead portion 92*b* and positioned near the proximal end 10*a* of the biosensor 10.

In the illustrated embodiment, the leads 72, 82, 92*a*, 92*b* extend generally along the length/of the biosensor 10 from the effective electrode portions 70, 80, 90*a*, 90*b* positioned within the capillary chamber 18 to the contacts 74, 84, 94*a*, 94*b*, respectively. The contacts 74, 84, 94*a*, 94*b* provide an electrical connection with a test meter (not shown) or another device when the biosensor 10 is coupled thereto. It is contemplated that the leads 72, 82, 92*a*, 92*b* extending from the effective electrode portions 70, 80, 90*a*, 90*b* can be configured to have any suitable shape, length or configuration, and may extend to any suitable location on the support substrate 12. It is further contemplated that the number and configuration of the effective electrode portions 70, 80, 90*a*, 90*b*, as well as the spacing between the effective electrode portions 70, 80, 90*a*, 90*b*, may be varied, and that the electrode arrangement 20 may include any number of electrodes and other types/configurations of electrodes other than those specifically illustrated and described herein. For example, alternative electrode arrangements are illustrated and described in U.S. Publication No. 2011/0186428, the contents of which are hereby incorporated herein in their entirety.

Referring collectively to FIGS. 3, 5*a*, 5*b* and 6, in the illustrated embodiment, the spacer substrate 14 has a rectangular configuration defining a length somewhat less than the length of the support substrate 12 and the overall length l of the biosensor 10 so as to expose the electrode contacts 74, 84, 94*a*, 94*b* of the electrodes 22, 24, 26, 26*b* for electrical connection with a test meter (not shown). The spacer substrate 14 also includes a bottom/lower surface or face 40, and a top/upper surface or face 42 facing a direction opposite the bottom/lower face 40. Additionally, the spacer substrate 14 includes opposite first and second end surfaces or edges 44*a*, 44*b* extending generally along the transverse axis T, and opposite first and second side surfaces or edges 46*a*, 46*b* extending generally along the longitudinal axis L and extending between the end surfaces 44*a*, 44*b*. While the end surfaces 44*a*, 44*b* and the side surfaces 46*a*, 46*b* of spacer substrate 14 are illustrated to form a generally rectangular shape, as indicated above, it should be understood that the biosensor 10, including the spacer substrate 14, may form other shapes and configurations without departing from the principles of the present invention.

Figure 3:
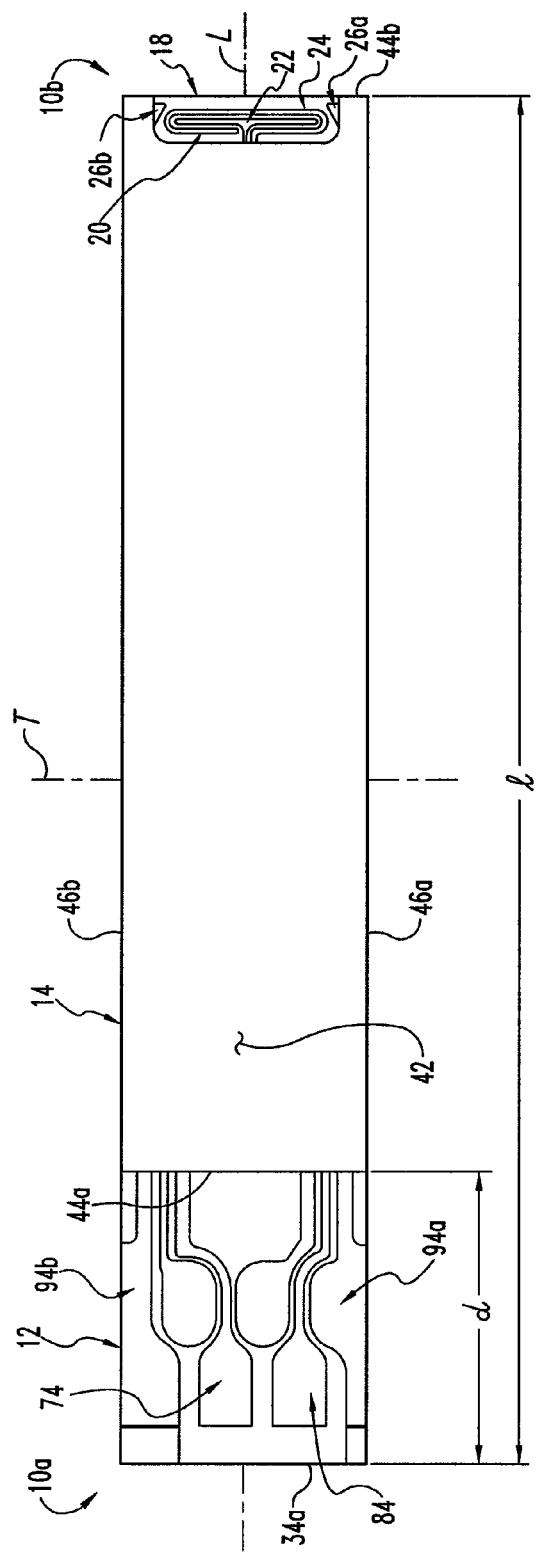
FIG. 3 is a top plan view of the biosensor of FIG. 2 with the hydrophilic roof removed.

Referring specifically to FIG. 3, the spacer substrate 14 is sized and configured to overlay the support substrate 12, with the side surfaces 46*a*, 46*b* of the spacer substrate 14 generally aligned with the side surfaces 36*a*, 36*b* of support substrate 12, and with the end surface 44*b* of the spacer substrate 14 generally aligned with the end surface 34*b* of support substrate 12. However, the end surface 44*a* of the spacer substrate 14 is axially offset/spaced from the end surface 34*a* of support substrate 12 by a distance d so as to not overlap the electrode contacts 74, 84, 94*a*, 94*b* on the support substrate 12 to thereby expose the electrode contacts 74, 84, 94a, 94b for electrical connection with a test meter (not shown).

Figure 5A:
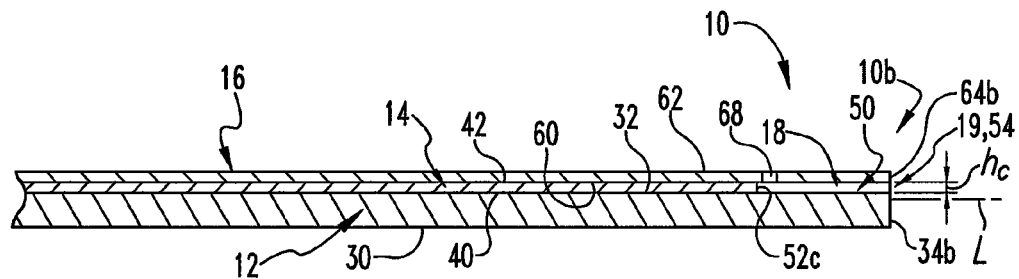
FIG. 5a is cross-sectional view of a portion of the biosensor of FIG. 1, as take along view line 5a-5a of FIG. 2.
Figure 5B:
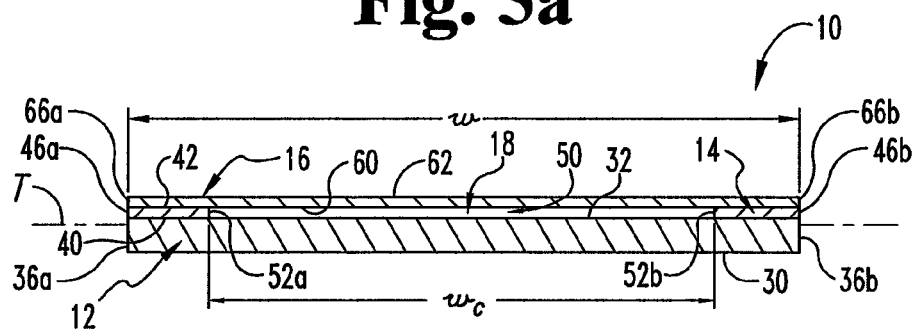
FIG. 5b is cross-sectional view of a portion of the biosensor of FIG. 1, as take along view line 5b-5b of FIG. 2.

Referring specifically to FIGS. 5a, 5b and 6, the spacer substrate 14 includes a generally rectangular-shaped notch or channel 50 extending entirely through the thickness of the spacer substrate 14 adjacent the end surface 44b. As will be discussed in further detail below, the channel 50 forms the inner boundary of the capillary chamber 18. In the illustrated embodiment, the channel 50 is defined by an inner edge or side wall 52 facing the capillary chamber 18. In the illustrated embodiment, the inner side wall 52 extends from the end surface 44b at a location adjacent the side surface 46a and back to the end surface 44b at a location adjacent the side surface 46b to thereby provide the channel 50 with a generally rectangular-shaped configuration. Additionally, in the illustrated embodiment, the inner side wall or edge 52 includes multiple edge portions or side walls 52a, 52b, 52c that extend along at least three sides of the capillary chamber 18 in a generally U-shaped pattern to define the inner outline or boundary of the capillary chamber 18, with the axial side walls 52a, 52b extending from the end surface 44b and generally along the longitudinal axis L, and with the lateral side wall 52c extending transversely between the axial side walls 52a, 52b. In the illustrated embodiment, the axial side walls 52a, 52b are interconnected with the lateral side wall 52c via a pair of rounded corners 52d, 52e. The channel 50 further defines an axially-facing opening 54 adjacent the end surface 44b, which in turn defines the sample inlet port 19 of the capillary chamber 18 adjacent the distal end 10b of the biosensor 10. The axial side walls 52a, 52b are separated or offset from one another to provide the capillary chamber 18 with a capillary chamber width $w_c$, and the lateral side wall 52c is offset from the end surface 44b to provide the capillary chamber 18 with a capillary chamber depth $d_c$. Additionally, the spacer substrate 14 has a thickness measured from the bottom/lower face 40 to the top/upper face 42 to provide the capillary chamber 18 with a capillary chamber height $h_c$.

Although the channel 50 has been illustrated and described as having a particular size, shape and configuration, it should be understood that other suitable sizes, shapes and configurations are also contemplated. For example, in other embodiments, the channel 50 may be provided with a non-rectangular configuration including, for example, a hemi-ovular configuration, a semi-circular configuration, a triangular configuration, or other suitable shapes and configurations. Additionally, various portions of the inner edge or side wall 52 of the channel 50 may be provided with a linear configuration, a curved or rounded configuration, a curvi-linear configuration and/or a polygonal configuration. In other embodiments, the opening 54 (and the corresponding sample inlet port 19) may be provided adjacent one of the side surfaces 46a, 46b of the spacer substrate 14, or adjacent the lower/bottom face 40 or the upper/top face 42 of the spacer substrate 14. Furthermore, in the illustrated embodiment, the spacer substrate 14 is configured as a single-piece, unitary spacer member. However, in other embodiments, the spacer substrate 14 can alternatively be comprised of a plurality of spacer members that are interconnected/integrated with one another to form the spacer substrate 14. In still other embodiments, the spacer substrate 14 need not necessarily include a channel 50 extending therethrough to define the inner boundary of the capillary chamber 18. For example, in other embodiments, an end surface or edge (i.e., the lateral side wall 52c) of the spacer substrate 14 may provide a single side wall defining the inner boundary of the capillary chamber 18. In other words, the spacer substrate 14 need not necessarily include the axial side walls 52a, 52b or the rounded corners 52d, 52e, but may instead provide a single side wall (i.e., the lateral side wall 52c) defining the inner boundary of the capillary chamber 18.

The spacer substrate 14 may formed from a wide variety of materials including an insulative material such as, for example, a flexible polymer such as an adhesive coated polyethylene terephthalate (PET)-polyester. A non-limiting example of a suitable material for the spacer substrate 14 includes a white PET film, with each of the bottom/lower and top/upper faces 40, 42 coated with a pressure-sensitive adhesive (PSA). However, it should be understood that other suitable materials and adhesives are also contemplated. It should also be understood that the bottom/lower face 40 of the spacer substrate 14 may be couple or fixed to the upper surface 32 of the support substrate 12 via the adhesive material. However, other suitable techniques/methods for coupling or fixing the spacer substrate 14 to the support substrate 12 are also contemplated including, for example, via heat or ultrasonic welding. As will be discussed in greater detail below, when the spacer substrate 14 is coupled to the support substrate 12, a portion of the top/upper surface of the support substrate 12 overlaps the capillary chamber 18 to thereby form a lower boundary of the capillary chamber 18.

When spacer substrate 14 is coupled to the support substrate 12, the effective electrode portions 70, 80, 90a, 90b of the electrode arrangement 20 are positioned to lie within the capillary chamber 18 which includes an inner boundary formed by the inner edge or side wall 52 of the spacer substrate 14 and the inwardly facing surfaces of the support substrate 12 and the cover substrate 16. As should be appreciated, any variation in the capillary chamber depth $d_c$ defined by the position of the lateral side wall 52c of the channel 50 relative to the end surface 44b may introduce variation in the effective area of the effective working electrode portion 70 located within the capillary chamber 18, thereby resulting in imprecision of the measured current value related to an analyte concentration. However, as will be discussed in detail below, the biosensor 10 is designed to minimize the effects of variations in the capillary chamber depth $d_c$, as well as the effective area of the effective working electrode portion 70 exposed to the capillary chamber 18 when the spacer substrate 14 is variably positioned relative to the support substrate 12.

Figure 2:
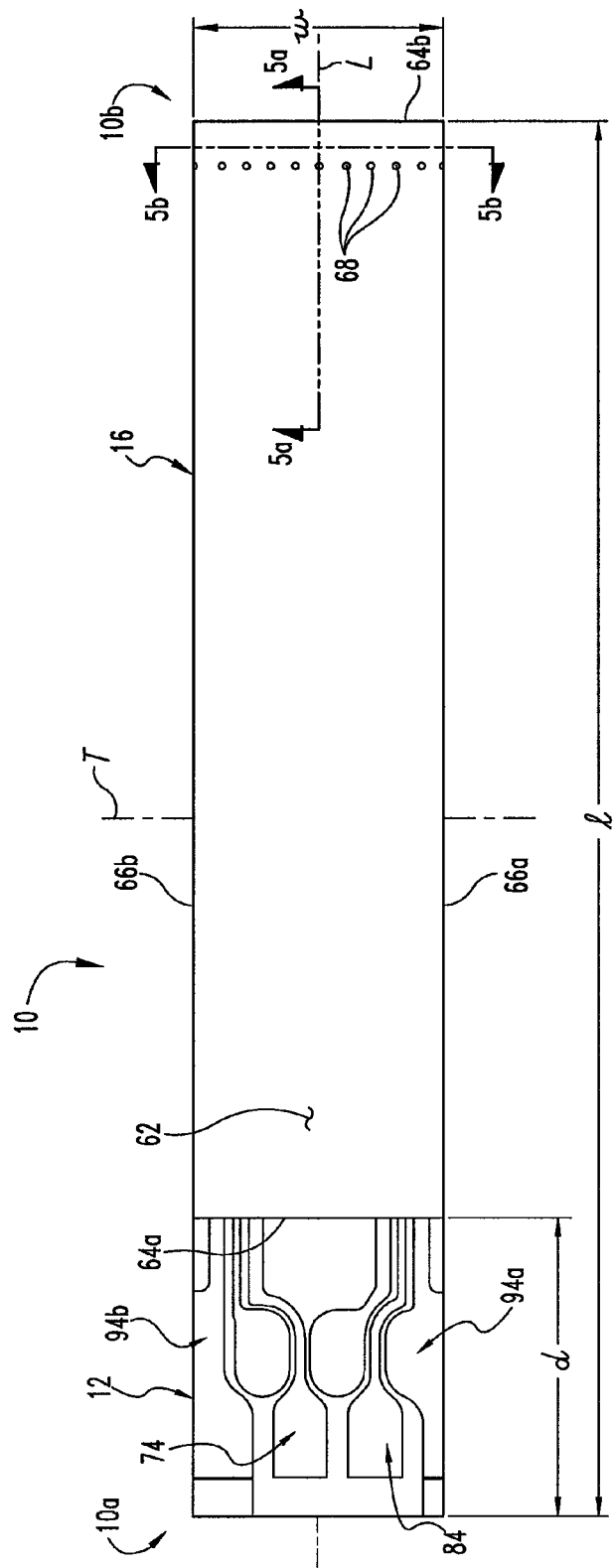
FIG. 2 is a top plan view of the biosensor of FIG. 1.

Referring collectively to FIGS. 2, 5a and 5b, in the illustrated embodiment, the cover substrate 16 has a rectangular configuration defining a length generally equal to the length of the spacer substrate 14, but somewhat less than the overall length/of the biosensor 10 so as to maintain exposure of the electrode contacts 74, 84, 94a, 94b for electrical connection with a test meter (not shown). The cover substrate 16 includes a bottom/lower surface 60 and a top/upper surface 62 facing a direction opposite the bottom/lower surface 60 and defining an outer surface of the biosensor 10. Additionally, the cover substrate 16 includes opposite first and second end surfaces or edges 64a, 64b, and opposite first and second side surfaces or edges 66a, 66b extending generally along the longitudinal axis L and extending between the end surfaces 64a, 64b. While the end surfaces 64a, 64b and the side surfaces 66a, 66b of the cover substrate 16 are illustrated to form a generally rectangular shape, as indicated above, it should be understood that the biosensor 10, including the cover substrate 16, may form other shapes and configurations without departing from the principles of the present invention.

As shown in FIGS. 5a and 5b, the cover substrate 16 is sized and configured to overlay the spacer substrate 14, with the side surfaces 66a, 66b of the cover substrate 16 generally aligned with the side surfaces 46a, 46b of the spacer substrate 14, and with the end surfaces 64a, 64b of the cover substrate 16 generally aligned with the end surfaces 44a, 44b of the spacer substrate 14. The cover substrate 16 may be formed from a wide variety of materials including a flexible polymer material such as, for example, a polyester or a polyimide. One non-limiting example of a suitable polymer material is a hydrophilic polyester film. However, other suitable polymer materials or non-polymer materials are also contemplated. The bottom/lower surface 60 may be couple or fixed to the top/upper face 42 of the spacer substrate 14 via the adhesive material associated with the spacer substrate 14. However, other suitable techniques/methods for coupling or fixing the cover substrate 16 to the spacer substrate 14 are also contemplated including, for example, via heat or ultrasonic welding. When the cover substrate 16 is coupled to the spacer substrate 14, a portion of the bottom/lower surface 60 of the cover substrate 16 overlaps the capillary chamber 18 to thereby form an upper boundary of the capillary chamber 18.

Additionally, in the illustrated embodiment, the cover substrate 16 defines a series of vent holes or apertures 68 extending through the cover substrate 16 from the top/upper surface 62 to the bottom/lower surface 60 and communicating with the capillary chamber 18. In one embodiment, the vent holes 68 are arranged in a linear manner adjacent the lateral side wall 52c of the channel 50 that forms an inner boundary of the capillary chamber 18. However, other suitable arrangements and positions of the vent holes 68 are also contemplated. As should be appreciated, the vent holes 68 serve as air outlets to vent air from the capillary chamber 18 as a fluid blood sample is drawn into the capillary chamber 18 via capillary action. Although the vent holes 68 are illustrated and described as being formed through the cover substrate 16, it should be understood that other embodiments are also contemplated where the vent holes 68 may be formed through portions of the support substrate 12 and/or the spacer substrate 14. In still other embodiments, the biosensor 10 need not necessarily include vent holes 68. For example, in alternative embodiments, other types and configurations of capillary structures as would be appreciated by those of skill in the art may be incorporated into the biosensor 10 to replace the vent holes, thereby eliminating the need for vent holes.

Referring specifically to FIGS. 5a and 5b, the capillary chamber 18 is bound/defined on the top and bottom by the bottom/lower surface 60 of the cover substrate 16 and the top/upper surface 32 of the support substrate 12, and is also bound/defined by the inner side wall 52 of the spacer substrate 14 to thereby define an inner boundary of the capillary chamber 18. The open end 54 of the channel 50 adjacent the end surfaces 44b of the spacer substrate 14 defines the sample inlet port 19 that opens into the capillary chamber 18 to permit entry of a fluid blood sample into the capillary chamber 18. Referring to FIG. 6, the effective electrode portions 70, 80, 90a, 90b are positioned within and in fluid communication with the capillary chamber 18. It is further contemplated that electrochemical reagents can be positioned within the capillary chamber 18 at or near the effective electrode portions 70, 80, 90a, 90b. The electrochemical reagents provide electrochemical probes for specific analytes. The choice of specific reagents depends on the specific analyte or analytes to be measured, the details of which are well known to those of ordinary skill in the art and therefore need not be discussed in detail herein. An example of a reagent that may be used in association with the biosensor 10 is a reagent for measuring glucose from a whole blood sample. However, it should be understood that other suitable reagents are also contemplated for use in association with the biosensor 10.

As indicated above, the working and counter electrodes 22, 24 have effective electrode portions 70, 80, respectively, positioned within and exposed to the capillary chamber 18. Referring to FIG. 6, shown therein is an arrangement of the effective working electrode portion 70 and the effective counter electrode portion 80 according to one embodiment of the present invention. As will be discussed in greater detail below, the arrangement and configuration of the effective working and counter electrode portions 70, 80 in combination with the configuration of other components of the biosensor 10 is designed: 1.) to maintain a balanced ratio between the effective working electrode area $A_w$ and the effective counter electrode area $A_c$ positioned within and exposed to the capillary chamber 18 as a result of imprecisions attributable to specification tolerances in the manufacturing of the biosensor 10; and 2.) to minimize variation in the absolute effective working electrode area $A_w$ as a result of imprecisions attributable to specification tolerances in the manufacturing of the biosensor 10. Additionally, it should be understood that the electrode features/characteristics attributable to satisfying these objectives allow for the use of positive and negative pulses to enable different types of measurement methods that reduce variation in the estimated blood glucose level, further details of which will be discussed below.

In the illustrated embodiment, the effective working electrode portion 70 includes a main body portion 76 and a single neck or leg portion 78 extending therefrom, and the effective counter electrode portion 80 includes a main body or loop portion 86 and a single neck or leg portion 88 extending therefrom. In one embodiment, the main body 76 of the effective working electrode portion 70 has a generally linear configuration extending along the capillary chamber width $w_c$ and arranged generally perpendicular to the longitudinal axis L of the biosensor 10, and the neck portion 78 extends from a mid-portion of the main body 76 along the capillary chamber depth $d_c$ and arranged generally along the longitudinal axis L to thereby provide the effective working electrode portion 70 with a generally T-shaped configuration having a pair of generally linear portions 76a, 76b extending in opposite directions relative to the neck portion 78. Additionally, in one embodiment, the main body or loop portion 86 of the effective counter electrode portion 80 has a generally C-shaped or looped configuration including generally linear portions 86a, 86b, 86c extending along the capillary chamber width $w_c$ and arranged generally perpendicular to the longitudinal axis L of the biosensor 10, a pair of rounded or arcuate portions 86d, 86e interconnecting the far ends of the linear portion 86a, 86b with the opposite ends of the linear portion 86c, and with the neck portion 88 extending from the near end of the linear portion 86a along the capillary chamber depth $d_c$ and arranged generally parallel with the longitudinal axis L. In the illustrated embodiment, the main body or loop 86 of the effective counter electrode portion 80 is positioned generally adjacent the main body 76 of the effective working electrode portion 70. More specifically, the main body or loop 86 of the effective counter electrode portion 80 wraps or extends peripherally about the main body 76 of the effective working electrode portion 70, with the neck portions 78, 88 arranged generally parallel with one another adjacent the longitudinal axis L and centrally positioned within the capillary chamber 18. As illustrated in FIG. 6, the corners defined by the outer edges of the effective working electrode portion 70 and the effective counter electrode portion 80 may be rounded to minimize electrical current concentrations that would otherwise be associated with sharp or non-rounded corners. As should be appreciated, such corners include those formed between the main body 76 and the neck 78, between the loop body 86 and the neck 88, and at the free ends of the main body 76 and the loop body 86. In one embodiment, the corners may be provided with a minimum radius of approximately 0.150 mm. Although specific shapes, configurations and arrangements of the effective working and counter electrode portions 70, 80 have been illustrated and described herein, it should be understood that other suitable shapes, configurations and arrangements are also contemplated as falling within the scope of the present invention.

In the illustrated embodiment, the main body 76 of the effective working electrode portion 70 has a generally uniform width $w_1$ along its length, and the neck 78 of the effective working electrode portion 70 has a generally uniform width $w_2$ along its length that is reduced/narrowed relative to the average width $w_1$ of the main body 76. In one embodiment, the width $w_2$ of the neck 78 is no more than 80% of the average width of the effective working electrode portion 70. In another embodiment, the width $w_2$ of the neck 78 is no more than one-half the average width of the effective working electrode portion 70. However, other ratios between the width $w_2$ of the working electrode neck 78 and the average width of the effective working electrode portion 70 are also contemplated. Additionally, the main body 86 of the effective counter electrode portion 80 has a generally uniform width $w_3$ along its length, and the neck 88 of the effective counter electrode portion 80 has a generally uniform width $w_4$ along its length that may be sized greater than, equal to, or less than the generally uniform width $w_3$ of the loop body 86. In the illustrated embodiment, the width $w_2$ of the working electrode neck 78 is less than the width $w_4$ of the counter electrode neck 88. In one embodiment, the width $w_2$ of the working electrode neck 78 is no more than one-half of the width $w_4$ of the counter electrode neck 88. In another embodiment, the width $w_2$ of the working electrode neck 78 is approximately 25-30% of the width $w_4$ of the counter electrode neck 88. However, other ratios between the width $w_2$ of the neck 78 and the width $w_4$ of the neck 88 are also contemplated. Additionally, in the illustrated embodiment, the spacing or offset distance s between the portions of the effective working electrode 70 and the adjacent portions of the effective counter electrode 80 is substantially uniform or constant along the entirety of the effective working and counter electrodes 70, 80. However, other embodiments are also contemplated where the spacing or offset distance between adjacent portions of the effective working and counter electrodes 70, 80 may vary in a non-uniform manner.

As indicated above, the effective working electrode portion 70 is provided with a single axially-extending neck 78 and the effective counter electrode portion 80 is likewise provided with a single axially-extending neck 88, with each of the necks 78, 88 extending generally parallel with one another adjacent the longitudinal axis L and centrally positioned within the capillary chamber 18. As should be appreciated, each of the necks 78, 88 extends across/intersects the inner edge or side wall 52 of the channel 50 that defines the inner boundary of the capillary chamber 18 at a single location, which in the illustrated embodiment constitutes the laterally-extending side wall 52c. As should also be appreciated, the axial location of the laterally-extending side wall 52c relative to the effective working and counter electrode portions 70, 80 may vary as a result of imprecisions attributable to tolerance specifications associated with the manufacturing process of the biosensor 10. Such imprecisions include but are not limited to variable axial placement of the spacer substrate 14 relative to the support substrate 12 (and the effective working and counter electrode portions 70, 80) along the longitudinal axis L, variations in the placement/size of the lateral side wall 52c of the spacer substrate 14, variations in the placement of the effective working and counter electrode portions 70, 80 on the support substrate 12, and/or other variations associated with the manufacturing and assembly of the biosensor 10. However, the manufacturing specifications associated with the biosensor 10 are determined to dictate/ensure that the sole portions of the effective working and counter electrode portions 70, 80 that extend across/intersect the laterally-extending side wall 52c (or any portion of the inner wall 52) of the capillary chamber 18 are the working and counter electrode necks 78, 88. In other words, the manufacturing specifications dictate/ensure that the laterally-extending side wall 52c (or any other portion of the inner side wall 52) does not intersect/overlap/cover any portion of the main bodies 76, 86 of the effective electrode portions 70, 80, thereby ensuring that the main bodies 76, 86 of the effective electrode portions 70, 80 are positioned entirely within the capillary chamber 18 and are not covered by any portion of the spacer substrate 14.

Figure 7B:
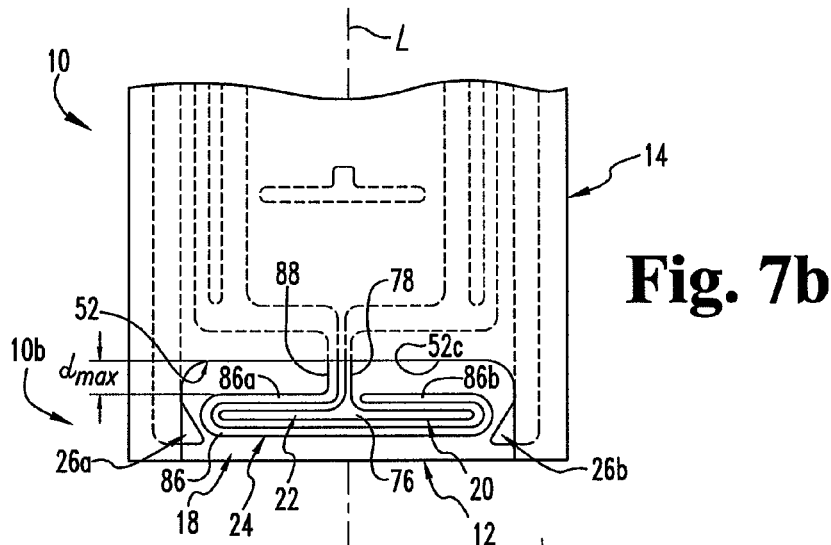
FIG. 7b is an enlarged plan view of the distal end portion of the biosensor of FIG. 1 illustrating a maximal placement of the spacer substrate relative to the support substrate and the electrode arrangement.
Figure 7A:
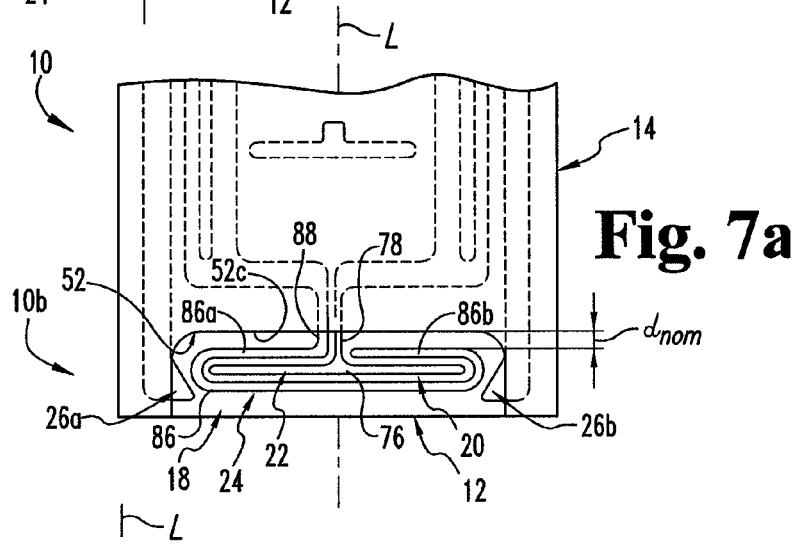
FIG. 7a is an enlarged plan view of the distal end portion of the biosensor of FIG. 1 illustrating a nominal placement of the spacer substrate relative to the support substrate and the electrode arrangement.
Figure 7C:
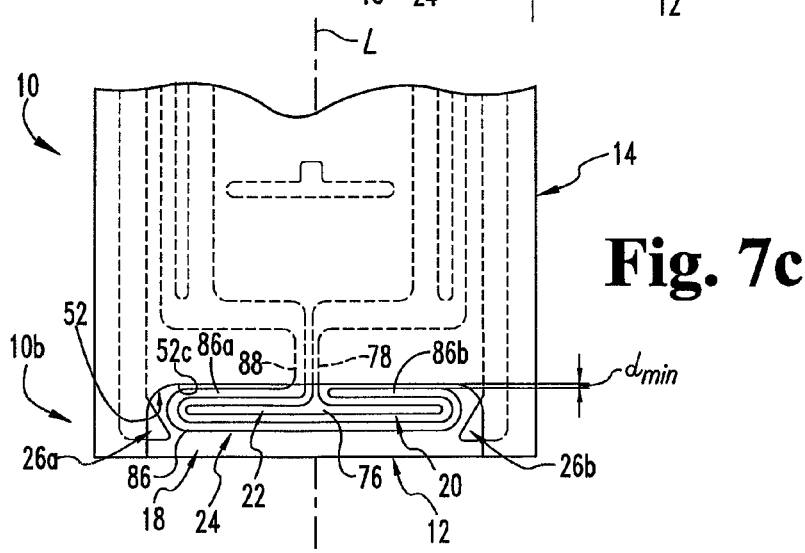
FIG. 7c is an enlarged plan view of the distal end portion of the biosensor of FIG. 1 illustrating a minimal placement of the spacer substrate relative to the support substrate and the electrode arrangement.

Referring to FIGS. 7a-7c, shown therein are three exemplary axial placements of the spacer substrate 14 relative to the support substrate 12 (and the capillary portions of the working and counter electrodes 22, 24 positioned in the capillary chamber 18) that may result from imprecisions associated with the manufacturing and assembly process of the biosensor 10. Specifically, FIG. 7a illustrates a nominal placement of the spacer substrate 14 relative to the support substrate 12 and the electrode arrangement 20 (i.e., the optimal specification tolerance limit on placement of the spacer substrate 14). In this nominal placement of the spacer substrate 12, each of the necks 78, 88 of the working and counter capillary electrodes 22, 24 extend across/intersect the inner boundary of the capillary chamber 18 at a single location (i.e., at the laterally-extending side wall 52c), and the main electrode bodies 76, 86 are positioned entirely within the capillary chamber 18 with the laterally-extending side wall 52c of the capillary chamber 18 spaced from the linear portions 86a, 86b of the effective counter electrode portion 80 at a nominal distance $d_{nom}$. FIG. 7b illustrates a maximal placement of the spacer substrate 14 relative to the support substrate 12 and the electrode arrangement 20 (i.e., the upper specification tolerance limit on placement of the spacer substrate 14). In this maximal placement of the spacer substrate 12, the electrode necks 78, 88 still extend across/intersect the inner boundary of the capillary chamber 18 at a single location, and the main electrode bodies 76, 86 are still positioned entirely within the capillary chamber 18, but the laterally-extending side wall 52c of the capillary chamber 18 is spaced from the linear portions 86a, 86b of the effective counter electrode portion 80 at a maximum distance $d_{max}$. FIG. 7c illustrates a minimal placement of the spacer substrate 14 relative to the support substrate 12 and the electrode arrangement 20 (i.e., the lower specification tolerance limit on placement of the spacer substrate 14). In this minimal placement of the spacer substrate 12, the electrode necks 78, 88 still extend across/intersect the inner boundary of the capillary chamber 18 at a single location, and the main electrode bodies 76, 86 are still positioned entirely within the capillary chamber 18, but the laterally-extending side wall 52c of the capillary chamber 18 is spaced from the main electrode bodies 76, 86 at a minimum distance $d_{min}$, which in the illustrated embodiment constitutes a substantially flush arrangement of the laterally-extending side wall 52c relative to the linear portions 86a, 86b of the effective counter electrode portion 80.

As should be appreciated, since the area of the effective working electrode portion 70 certain to be positioned within the capillary chamber 18 is significantly greater than the potential variance in the area of the neck 78 positioned within the capillary chamber 18 resulting from acceptable tolerance levels associated with imprecisions in the manufacturing process, variations in the effective working electrode area $A_w$ of the effective working electrode portion 70 exposed to the capillary chamber 18 is minimized, thereby resulting in improved measurement precision and/or accuracy of the biosensor 10. This minimization of the variation in the effective working electrode area $A_w$ is primarily attributable to the reduced/narrowed width $w_2$ of the neck 78 relative to the average width of the effective electrode portion 70 (i.e., minimization of the change in the area of the neck 78 along the reduced/narrowed width $w_2$ per unit length of the neck 78), and the assurance that the sole portion of the effective working electrode portion that extends across/intersects the inner boundary of capillary chamber 18 (i.e., the inner side wall 52) is the reduced/narrowed width $w_2$ of the single neck 78 that extends across/intersects the laterally-extending side wall 52c.

As should also be appreciated, since the effective working and counter electrode areas ($A_w$, $A_c$) of the effective working and counter electrode portions 70, 80 certain to be positioned within the capillary chamber 18 is significantly greater than the potential variance in the areas of the necks 78, 88 positioned within the capillary chamber 18 resulting from acceptable tolerance levels associated with imprecisions in the manufacturing process of the biosensor 10, a relatively constant/uniform ratio R between the effective counter electrode area $A_c$ and the effective working electrode area $A_w$ exposed to the capillary chamber 18 can be maintained, which likewise results in improved measurement precision and/or accuracy of the biosensor 10.

The general meaning of the term "relatively constant" (when used in association with ratio R) is that for given uses of biosensors embodying the present invention, maintaining ratio R as uniform or otherwise absolutely constant is not necessary in contexts in which a certain amount of tolerance is acceptable. For example, in the context of the biosensor 10 illustrated in FIGS. 7a-7c, if the minimal spacer position is adjusted such that the inner boundary of the capillary chamber overlaps the electrode necks 78, 88 at a portion where one or both of the necks 78, 88 begin to radius outwardly to the main body 76, 86 of each electrode, respectively, then ratio R cannot be maintained uniformly. Nevertheless, the difference between ratio R at the nominal and maximal spacer positions and the ratio R at the minimal spacer position is relatively constant, and may still be acceptable depending on the degree of accuracy required for the particular use of the biosensor 10.

In order to maintain a relatively constant/uniform ratio R between the effective counter electrode area $A_c$ and the effective working electrode area $A_w$ (i.e., $R=A_c/A_w$) in view of the acceptable tolerance levels associated with the manufacturing process of the biosensor 10, the following formula may be applied to provide parameters regarding the configuration/design of the working and counter electrodes: $A_c/w_4=A_w/w_2$ (where $A_c$ is the effective counter electrode area, $w_4$ is the width of the counter electrode neck 88, $A_w$ is the effective working electrode area, and $w_2$ is the width of the working electrode neck 78).

It should be understood that the effective working electrode area $A_w$ and the effective counter electrode area $A_c$ are defined as the respective areas of the effective working and counter electrode portions 70, 80 exposed to the capillary chamber 18 and in contact with a fluid blood sample in the capillary chamber 18 when the capillary chamber 18 contains a sufficient volume of the fluid blood sample to initiate a measurement sequence. It should also be understood that the widths $w_2$, $w_4$ of the working and counter electrode necks 78, 88 are defined as the widths of the necks 78, 88 that are intersected/overlapped by inner boundary of the capillary chamber 18 (i.e., the laterally-extending side wall 52c).

In the illustrated embodiment, the sample sufficiency electrodes 26a, 26b are configured as working and counter sample sufficiency electrodes, and are configured as substantially mirror images of one another relative to the longitudinal axis L. However, it should be understood that other embodiments are also contemplated wherein the sample sufficiency electrodes 26a, 26b are provided with different configurations. In still other embodiments, the sample sufficiency electrodes 26a, 26b are optional and are not included in the biosensor 10. In one embodiment, the sample sufficiency electrodes 26a comprises a working sample sufficiency electrode, and the sample sufficiency electrodes 26b comprises a counter sample sufficiency electrode. However, a reverse configuration is also contemplated. As shown in the FIG. 6, the effective sample sufficiency electrode portions 90a, 90b of the sample sufficiency electrodes 26a, 26b each have a generally triangular-shaped cross section that extends into the capillary chamber 18 from opposite sides of the capillary chamber 18. In the illustrated embodiment, the triangular-shaped effective electrode portions 90a, 90b each have a side surface 96a arranged at an obtuse angle relative to the longitudinal axis L, and an end surface 96b extending from the side surface 96a and arranged generally perpendicular to the longitudinal axis L. However, other suitable shapes and configurations of the capillary electrode portions 90a, 90b are also contemplated. As set forth herein, the sample sufficiency electrodes 26a, 26b are configured to detect when a sufficient volume of a liquid blood sample is received within the capillary chamber 18.

In use, a number of the biosensors 10 are typically packaged in a vial that usually includes a stopper or cap configured to seal the vial. It should be appreciated, however, that the biosensors may be packaged individually, or biosensors 10 can be folded upon one another, rolled in a coil, stacked in a cassette magazine, or packed in blister packaging. In another embodiment, the packaging may be formed as a card with removable individual segments comprised of biosensors, examples of which may be found in U.S. patent application Ser. No. 12/198,197, the contents of which are incorporated herein by reference in their entirety.

Many fluid sample types may be analyzed using the biosensor 10 discussed herein. For example, human body fluids such as, for example, whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues can also be assayed, along with foods, fermentation products and environmental substances, which potentially contain environmental contaminants. Whole blood may be assayed with the biosensor 10.

A user of the biosensor 10 initially places a finger having a blood collection incision or puncture adjacent/against the sample inlet port 19 to the capillary chamber 18. Capillary forces pull a liquid blood sample from the incision or puncture through the sample inlet port 19 and into the capillary chamber 18 and across the reagents and the electrode arrangement 20 located in the capillary chamber 18. The liquid blood sample dissolves the reagents and engages the electrode arrangement 20 in the capillary chamber 18 where an electrochemical reaction takes place. In embodiments of the biosensor 10 including the sample sufficiency electrodes 26a, 26b, a signal is generated when the liquid blood sample in the capillary chamber 18 contacts the effective electrode portions 90a, 90b, thereby indicating that a sufficient volume of the liquid blood sample has been received in the capillary chamber 18. Sometime after the reaction has begun, a power source (e.g., a battery) applies a potential difference between the working and counter electrodes 22, 24. When the potential difference is applied, the amount of oxidized form of the mediator at the counter electrode 24 and the potential difference must be sufficient to cause electro-oxidation of the reduced form of the mediator at the surface of the working electrode 22. A current measuring meter (not shown) measures the current generated by the oxidation of the reduced form of the mediator at the surface of the working electrode 22.

As indicated above, the biosensor 10 disclosed herein is configured to minimize variations in the effective working electrode area $A_w$ exposed to the capillary chamber 18, and also maintains a relatively constant/uniform ratio R between the effective counter electrode area $A_c$ and the effective working electrode area $A_w$ exposed to the capillary chamber 18, thereby resulting in improvements to the precision and/or accuracy of the biosensor 10, and more particularly to improved precision and/or accuracy of measured blood glucose levels. It should be appreciated that such improvements to the precision and/or accuracy of the biosensor 10 resulting from the unique configuration and features associated with the working and counter electrodes 22, 24 and other structures/features associated with the biosensor 10 are particularly apparent in biosensor applications involving the use of both positive and negative pulsed signals between the working and counter electrodes 22, 24 in the sensing/measurement process to enable ascorbate detection and measurement of blood glucose levels. Such positive/negative pulsed signals may be realized via the positive/negative pulses inherent in AC signals, and/or positive/negative pulses that may stem from the use of varied DC signals exhibiting positive and negative polarity. However, it should be understood that in other embodiments, the biosensor 10 need not necessarily be used in applications involving pulsed signals.

Figure 8B:
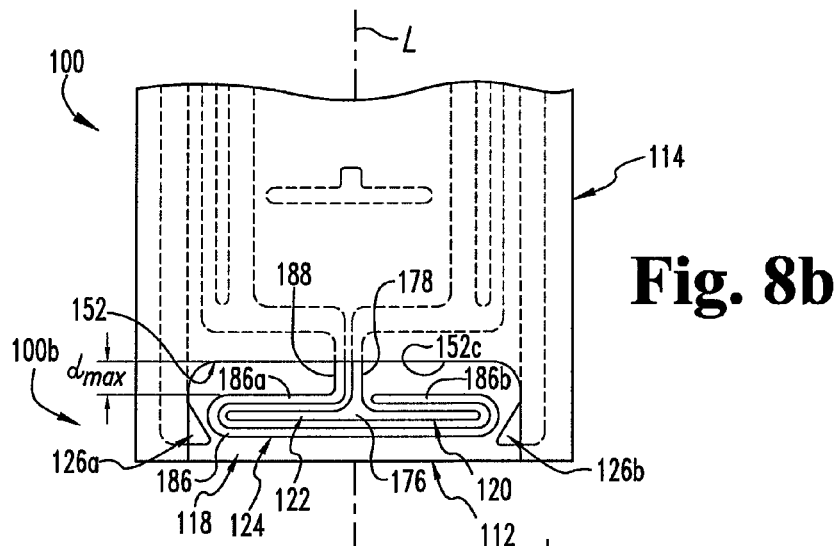
FIG. 8b is an enlarged plan view of the distal end portion of the comparative biosensor illustrating a maximal placement of the spacer substrate relative to the support substrate and the electrode arrangement.
Figure 8A:
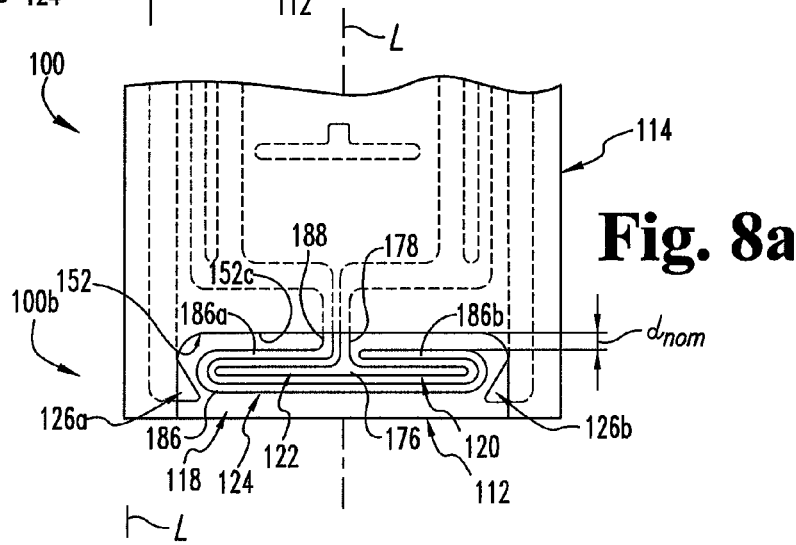
FIG. 8a is an enlarged plan view of a distal end portion of a comparative biosensor illustrating a nominal placement of a spacer substrate relative to a support substrate and an electrode arrangement.
Figure 8C:
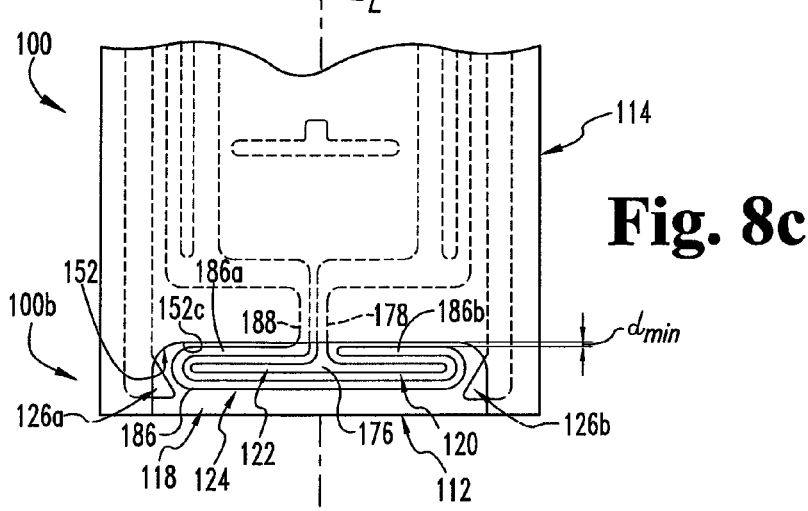
FIG. 8c is an enlarged plan view of the distal end portion of the comparative biosensor illustrating a minimal placement of the spacer substrate relative to the support substrate and the electrode arrangement.

Referring to FIGS. 8a-8c, illustrated therein is a first comparative biosensor 100 including many of the same elements and features illustrated and described above with regard to the biosensor 10. For example, the comparative biosensor 100 has a proximal end (not shown) and an opposite distal end 100b arranged along a longitudinal axis L, and generally includes an electrode support substrate 112, an intermediate spacer substrate 114 positioned on the support substrate 112, and a cover substrate or hydrophilic roof (not shown) positioned on the spacer substrate 114. The support substrate 112, the spacer substrate 114 and the cover substrate cooperate with one another to define a capillary chamber or channel 118 having a sample inlet port for receiving a fluid sample adjacent the distal end 100b of the biosensor 100. Additionally, the support substrate 112 includes an electrical conductor arrangement 120 including a series of electrodes 122, 124, 126a and 126b that each include one or more electrode portions positioned within the capillary chamber 118. In the illustrated embodiment, the electrode 122 is configured as a working electrode, the electrode 124 is configured as a reference or counter electrode, and the electrodes 126a, 126b are configured as sample sufficiency electrodes.

In the illustrated embodiment, the working electrode 122 includes an effective working electrode portion exposed to the capillary chamber 118 having a main body portion 176 and a single neck or leg portion 178 extending therefrom to thereby define a generally T-shaped configuration, and the counter electrode 124 includes an effective counter electrode portion having a main body or loop portion 186 positioned generally adjacent the main body 176 of the effective working electrode portion, and more specifically defining a generally C-shaped or looped configuration that wraps or extends peripherally about the main body 176 of the effective working electrode portion and also having a single neck or leg portion 188 extending from the main body 186. However, unlike the biosensor 10 illustrated and described above, the body portion 176 and the neck portion 178 of the working electrode 122 have a substantially equal/uniform electrode width (i.e., the width of the neck 178 is not reduced relative to the main body 176). Additionally, the neck portion 178 of the working electrode 122 has a width that is substantially equal to the width of the neck portion 188 of the counter electrode 124. It should be appreciated that other than the increased width of the working electrode neck 178, the biosensor 100 is configured substantially identical to the biosensor illustrated and described above.

FIGS. 8a-8c illustrate three exemplary axial placements of the spacer substrate 114 relative to the support substrate 112 (and relative to the effective portions of the working and counter electrodes 122, 124 positioned in the capillary chamber 118) that may result from imprecisions associated with the manufacturing and assembly process of the biosensor 100. It should be appreciated that the exemplary axial placements of the spacer substrate 114 relative to the support substrate 112 illustrated in FIGS. 8a-8c correspond to the exemplary axial placements of the spacer substrate 14 relative to the support substrate 12 illustrated and described above with regard to FIGS. 7a-7c.

Referring specifically to FIG. 8a, illustrated therein is a nominal placement of the spacer substrate 114 relative to the support substrate 112 and the electrode arrangement 120. In this nominal placement, the necks 178, 188 of the working and counter capillary electrodes 122, 124 extend across/intersect the inner boundary of the capillary chamber 118 at a single location (i.e., at the laterally-extending side wall 152c), and the main electrode bodies 176, 186 are positioned entirely within the capillary chamber 118 with the laterally-extending side wall 152c of the capillary chamber 118 spaced from the linear portions 186a, 186b of the effective counter electrode portion at a nominal distance $d_{nom}$. FIG. 8b illustrates a maximal placement of the spacer substrate 114 relative to the support substrate 112 and the electrode arrangement 120 wherein the electrode necks 178, 188 extend across/intersect the inner boundary of the capillary chamber 118 at a single location, and the main electrode bodies 176, 186 are positioned entirely within the capillary chamber 18, but the laterally-extending side wall 152c of the capillary chamber 118 is spaced from the linear portions 186a, 186b of the effective counter electrode portion at a maximum distance $d_{max}$. FIG. 8c illustrates a minimal placement of the spacer substrate 114 relative to the support substrate 112 and the electrode arrangement 120 wherein the electrode necks 178, 188 extend across/intersect the inner boundary of the capillary chamber 118 at a single location, and the main electrode bodies 176, 186 are positioned entirely within the capillary chamber 118, but the laterally-extending side wall 152c of the capillary chamber 118 is spaced from the main electrode bodies 176, 186 at a minimum distance $d_{min}$, which in the illustrated embodiment constitutes a substantially flush arrangement of the laterally-extending side wall 152c relative to the linear portions 186a, 186b of the effective counter electrode portion.

Figure 9B:
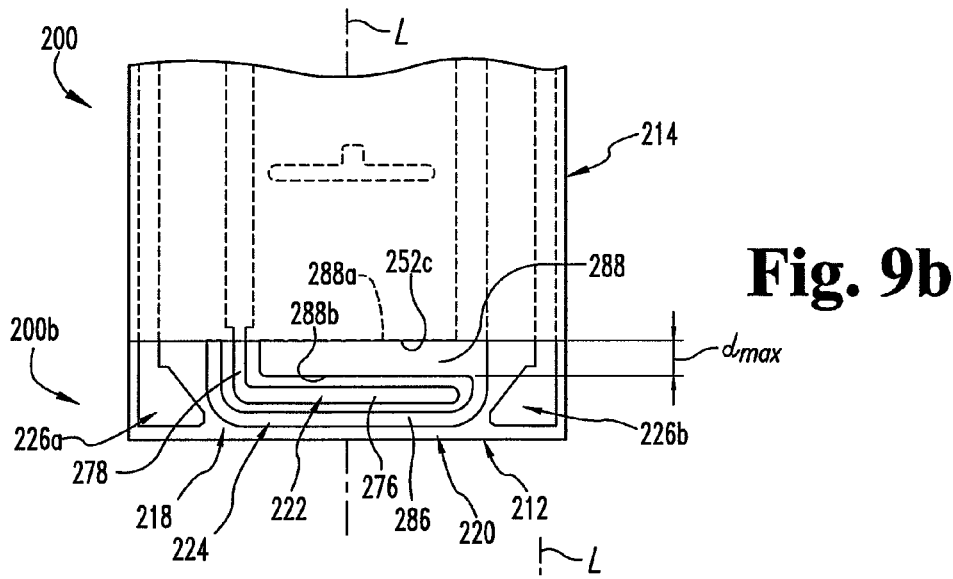
FIG. 9b is an enlarged plan view of the distal end portion of the second comparative biosensor illustrating a maximal placement of the spacer substrate relative to the support substrate and the electrode arrangement.
Figure 9A:
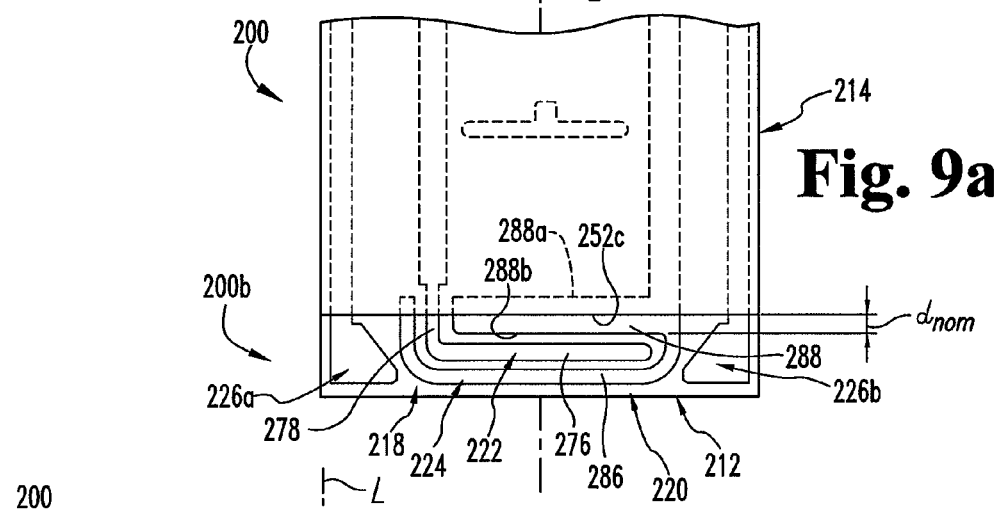
FIG. 9a is an enlarged plan view of a distal end portion of a second comparative biosensor illustrating a nominal placement of a spacer substrate relative to a support substrate and an electrode arrangement.
Figure 9C:
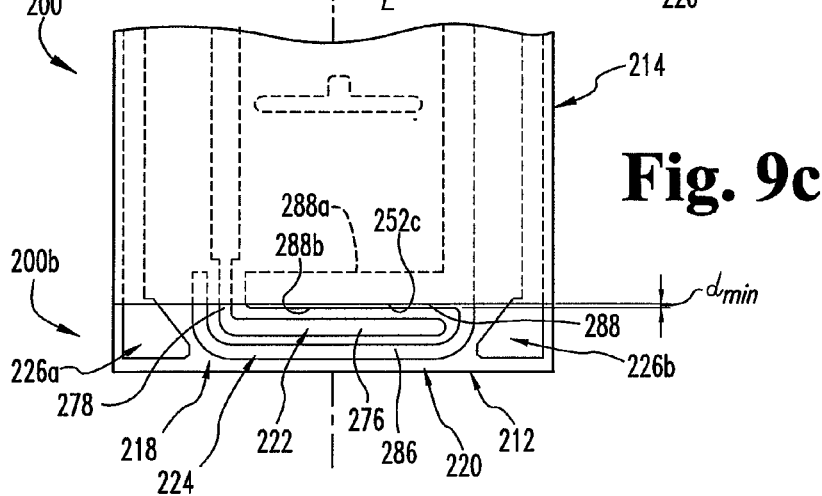
FIG. 9c is an enlarged plan view of the distal end portion of the second comparative bio sensor illustrating a minimal placement of the spacer substrate relative to the support substrate and the electrode arrangement.

Referring to FIGS. 9a-9c, illustrated therein is a second comparative biosensor 200 including some of the same elements and features illustrated and described above with regard to the biosensor 10, but having a different configuration and layout relative to the biosensor 10. In the illustrated embodiment, the comparative biosensor 200 has a proximal end (not shown) and an opposite distal end 200b arranged along a longitudinal axis L, and generally includes an electrode support substrate 212 and an intermediate spacer substrate 214 positioned on the support substrate 212. The comparative biosensor 200 may further include a cover substrate or hydrophilic roof (not shown) positioned on the spacer substrate 214. The support substrate 212, the spacer substrate 214 and the cover substrate cooperate with one another to define a capillary chamber or channel 218 having a sample inlet port for receiving a fluid sample adjacent the distal end 200b of the biosensor 200. Additionally, the support substrate 212 includes an electrical conductor arrangement 220 including a series of electrodes 222, 224, 226a and 226b that each include one or more electrode portions positioned within the capillary chamber 218. In the illustrated embodiment, the electrode 222 is configured as a working electrode, the electrode 224 is configured as a reference or counter electrode, and the electrodes 226a, 226b are configured as sample sufficiency electrodes.

Unlike the biosensor 10 which includes a capillary chamber 18 having a generally U-shaped configuration (i.e., bound by a pair of axial side walls 52a, 52b and a lateral side wall 52c which together define the inner boundary of the capillary chamber 18), the capillary chamber 218 of the biosensor 200 extends across the entire width of the support substrate 212. In this embodiment, the distal edge of the spacer substrate 214 provides a laterally-extending side wall 252c defining an inner boundary of the capillary chamber 218. However, other configurations are also possible, including embodiments similar to the biosensor 10 where the capillary chamber defines a generally U-shaped configuration.

In the illustrated embodiment, the working electrode 222 includes an effective working electrode portion exposed to the capillary chamber 218 and having a main body portion 276 and a single neck or leg portion 278 extending from an end of the main body portion 276 to thereby define a generally L-shaped electrode configuration. Like the biosensor 10 illustrated and described above, the effective working electrode portion includes a single neck portion that extends across/intersect the inner boundary of the capillary chamber 218 at a single location (i.e., at the laterally-extending side wall 252c). Additionally, in the illustrated embodiment, the counter electrode 224 includes an effective counter electrode portion exposed to the capillary chamber 218 and having a first arm portion 286 defining a generally U-shaped configuration that extends or wraps about a distal side of the main body portion 276 of the effective working electrode portion, and a second arm portion 288 defining a generally linear configuration extending along a proximal side of the main body portion 276 and arranged generally parallel with the main body portion 276. More specifically, the first arm portion 286 and the second arm portion 288 together provide the effective counter electrode portion with a looped configuration that wraps or extends peripherally about and encloses the main body portion 276 and the neck portion 278 of the effective working electrode. However, unlike the biosensor 10 illustrated and described above, the effective counter electrode does not include a single neck portion that extends across/intersect the inner boundary of the capillary chamber 218 at a single location (i.e., at the laterally-extending side wall 252c). Instead, the end of the first arm portion 286 and the entire length of the second arm portion 288 extend across/intersect the inner boundary of the capillary chamber 218 at the laterally-extending side wall 252c.

FIGS. 9a-9c illustrate three exemplary axial placements of the spacer substrate 214 relative to the support substrate 212 (and relative to the effective portions of the working and counter electrodes 222, 224 positioned in the capillary chamber 218) that may result from imprecisions associated with the manufacturing and assembly process of the biosensor 200. It should be appreciated that the exemplary axial placements of the spacer substrate 214 relative to the support substrate 212 illustrated in FIGS. 9a-9c correspond to the exemplary axial placements of the spacer substrate 14 relative to the support substrate 12 illustrated and described above with regard to FIGS. 7a-7c.

Referring specifically to FIG. 9a, illustrated therein is a nominal placement of the spacer substrate 214 relative to the support substrate 212 and the electrode arrangement 220. In this nominal placement, the neck 278 of the working electrode 222 extends across/intersects the inner boundary of the capillary chamber 218 at a single location (i.e., at the laterally-extending side wall 252c). However, the counter electrode 224 extends across/intersects the inner boundary of the capillary chamber 218 at multiple locations. More specifically, the first and second arm portions 286, 288 of the counter electrode 224 each extend across/intersect the inner boundary of the capillary chamber 218 at the laterally-extending side wall 252c. Additionally, while the main body portion 276 of the working electrode 222 is positioned entirely within the capillary chamber 218, portions of the first and second arm portions 286, 288 of the counter electrode 224 extend outside of the capillary chamber 218.

As illustrated in FIG. 9a, nominal placement of the spacer substrate 214 relative to the support substrate 212 results in the laterally-extending side wall 252c of the capillary chamber 218 (i.e., the distal edge of the spacer substrate 214) being spaced from the distal side 288b of the second arm portion 288 of the counter electrode 224 at a nominal distance $d_{nom}$. As illustrated in FIG. 9b, maximal placement of the spacer substrate 214 relative to the support substrate 212 results in the laterally-extending side wall 252c of the capillary chamber 218 (i.e., the distal edge of the spacer substrate 214) being spaced from the distal side 288b of the second arm portion 288 at a maximum distance $d_{max}$, which in the illustrated embodiment constitutes a substantially flush arrangement of the laterally-extending side wall 252c relative to the proximal side 288a of the second arm portion 288 of the counter electrode 224. As illustrated in FIG. 9c, minimal placement of the spacer substrate 214 relative to the support substrate 212 results in the laterally-extending side wall 252c of the capillary chamber 218 (i.e., the distal edge of the spacer substrate 214) being spaced from the distal side 288b of the second arm portion 288 at a minimum distance $d_{min}$, which in the illustrated embodiment constitutes a substantially flush arrangement of the laterally-extending side wall 252c relative to the distal side 288b of the second arm portion 288 of the counter electrode 224.

For purposes of comparing the features, attributes and characteristics associated with the biosensor 10 relative to the comparative biosensors 100 and 200, Table A sets forth data associated with the biosensor 10 in the three exemplary configurations illustrated in FIGS. 7a-7c (i.e., the nominal, maximum, minimum positions of the spacer substrate 14), Table B sets forth data associated with the comparative biosensor 100 in the three exemplary configurations illustrated in FIGS. 8a-8c (i.e., the nominal, maximum, minimum positions of the spacer substrate 114), and Table C sets forth data associated with the comparative biosensor 200 in the three exemplary configurations illustrated in FIGS. 9a-9c (i.e., the nominal, maximum, minimum positions of the spacer substrate 214). It should be understood that the data set forth in Tables A, B and C is exemplary in nature, and does not in any way limit the scope of the present invention.

Referring to Table A below in combination with FIGS. 7a-7c, as indicated above, the biosensor 10 is designed and configured to minimize variations in the effective working electrode area $A_w$ of the working electrode 22 exposed to the capillary chamber 18 in view of acceptable tolerance levels associated with manufacturing of the biosensor 10. Additionally, the biosensor 10 is also designed and configured to maintain a relatively constant/uniform ratio R between the effective counter electrode area $A_c$ of the counter electrode 24 exposed to the capillary chamber 18 and the effective working electrode area $A_w$ of the working electrode 22 exposed to the capillary chamber 18 (i.e., $R=A_c/A_w$) in view of the acceptable tolerance levels associated with manufacturing of the biosensor 10.

With regard to minimizing variations in the effective working electrode area $A_w$ of the working electrode 22, the biosensor 10 is designed and configured to minimize such variations as the position/placement of the inner boundary of the capillary chamber 18 (i.e., the inner side wall 52c) is varied between the nominal tolerance position illustrated in FIG. 7a and the maximum and minimum tolerance positions illustrated in FIGS. 7b and 7c, respectively. As indicated above, since the effective working electrode area $A_w$ positioned within the capillary chamber 18 is significantly greater than the variance in the area of the neck 78 positioned within the capillary chamber 18 as the position of the inner boundary of the capillary chamber 18 is varied between the nominal, maximum and minimum tolerance positions, variance in the effective working electrode area $A_w$ is minimized. This minimization in the variation of the effective working electrode area $A_w$ is at least partially attributable to the reduced/narrowed width of the neck 78 relative to the width of the main body 76 of the effective working electrode (i.e., minimization of the change in the area of the neck 78 per unit length of the neck 78), as well as limiting the portion of the working electrode 22 that intersects the variable inner boundary (i.e., the inner side wall 52c) of the capillary chamber 18 to the reduced/narrowed width of the working electrode neck 78.

As illustrated in Table A, in the exemplary embodiment of the biosensor 10, the variation of the effective working electrode area $A_w$ between the nominal and the maximum spacer positions is +2.60%, and the variation of the effective working electrode area $A_w$ between the nominal and the minimum spacer positions is −2.60%. Additionally, the overall variation of the effective working electrode area $A_w$ between the maximum and minimum spacer positions is +5.07%. In this exemplary embodiment, the width of the working electrode neck 78 is 0.050 mm, the width of the counter electrode neck 88 is 0.107 mm, the width of the working electrode main body 76 is 0.100 mm, and the width of the counter electrode main body 86 is 0.100 mm. Additionally, the nominal distance $d_{nom}$ is 1.000 mm, the maximum distance $d_{max}$ is 1.165 mm, and the minimum distance $d_{min}$ is 0.835 mm. However, it should be understood that these values are exemplary in nature and do not in any way limit the scope of the present invention. As should be appreciated, minimizing variations in the effective working electrode area $A_w$ as the position/placement of the inner boundary of the capillary chamber 18 is varied due to tolerance levels associated with manufacturing of the biosensor 10 results in perceptible improvements in the precision and/or accuracy of the biosensor 10, which in turn results in improved precision and/or accuracy of measured blood glucose levels.

With regard to maintaining a relatively constant/uniform ratio R between the effective counter electrode area $A_c$ of the counter electrode 24 and the effective working electrode area $A_w$ of the working electrode 22, the biosensor 10 is designed and configured to substantially maintain the area ratio R as the position/placement of the inner boundary of the capillary chamber 18 (i.e., the inner side wall 52c) is varied between the nominal tolerance position illustrated in FIG. 7a and the maximum and minimum tolerance positions illustrated in FIGS. 7b and 7c, respectively. As indicated above, the biosensor 10 and the size/shape/configuration of the effective portions of the working and counter electrodes 22, 24 are specifically designed such that the ratio R between the effective electrode areas $A_c$, $A_w$ is substantially maintained as the position of the inner boundary of the capillary chamber 18 is varied between the nominal, maximum and minimum tolerance positions. Maintaining a relatively constant/uniform ratio R is at least partially attributable to the reduced/narrowed width of the working electrode neck 78 relative to the width of the counter electrode neck 88, the

TABLE A

| | Effective Counter Electrode Area $A_C$ (mm²) | Effective Working Electrode Area $A_W$ (mm²) | % Variation of WE Area $A_W$ (from nominal) | Area Ratio $R = A_C/A_W$ | % Variation of Area Ratio R (from nominal) |
|---|---|---|---|---|---|
| Nominal Spacer Position ($d_{nom}$) | 0.68099 | 0.31751 | — | 2.145 | — |
| Maximum Spacer Position ($d_{max}$) | 0.69865 | 0.32576 | +2.60% | 2.145 | 0.00% |
| Minimum spacer Position ($d_{min}$) | 0.66332 | 0.30926 | −2.60% | 2.145 | 0.00% | reduced effective working electrode areas $A_w$ relative to the effective counter electrode areas $A_c$, as well as limiting the portions of the working and counter electrodes 22, 24 that intersects the variable inner boundary of the capillary chamber 18 to the working and counter electrode necks 78, 88.

maintain a relatively constant/uniform ratio R between the effective counter electrode area $A_c$ and the effective working electrode area $A_w$ as the position/placement of the inner boundary of the capillary chamber 118 is varied between the tolerance positions illustrated in FIGS. 8a-8c.

TABLE B

|  | Effective Counter Electrode Area $A_C$ (mm²) | Effective Working Electrode Area $A_W$ (mm²) | % Variation of WE Area $A_W$ (from nominal) | Area Ratio $R = A_C/A_W$ | % Variation of Area Ratio R (from nominal) |
|---|---|---|---|---|---|
| Nominal Spacer Position ($d_{nom}$) | 0.67459 | 0.33751 | — | 1.999 | — |
| Maximum Spacer Position ($d_{max}$) | 0.69109 | 0.35401 | +4.89% | 1.952 | −2.35% |
| Minimum spacer Position ($d_{min}$) | 0.65808 | 0.32101 | −4.89% | 2.050 | +2.55% |

As illustrated in Table A, in one embodiment, the variation in the area ratio R (i.e., $A_c/A_w$) between the nominal and the maximum spacer positions is 0.00%, and the variation in the area ratio R between the nominal and the minimum spacer positions is also 0.00%. Additionally, the overall variation in the area ratio R between the maximum and minimum spacer positions is likewise 0.00%. As discussed above, maintaining a relatively constant/uniform ratio R between the effective counter electrode area $A_c$ and the effective working electrode area $A_w$ as the position/placement of the inner boundary of the capillary chamber 18 is varied due to tolerance levels associated with manufacturing of the biosensor 10 results in perceptible improvements in the precision and/or accuracy of the biosensor 10, which in turn results in improved precision and/or accuracy of measured blood glucose levels. As should be appreciated, the illustrated embodiment of the biosensor 10 exhibits a perfectly constant/uniform ratio R between the effective counter electrode area $A_c$ and the effective working electrode area $A_w$ as the position/placement of the inner boundary of the capillary chamber 18 is varied due to tolerance levels associated with manufacturing of the biosensor 10. However, it should be appreciated that other embodiments of the biosensor 10 are also contemplated where the biosensor exhibits a relatively constant/uniform ratio R between the effective counter electrode area $A_c$ and the effective working electrode area $A_w$.

Referring to Table B below in combination with FIGS. 8a-8c, shown therein is data associated with the comparative biosensor 100. As indicated above, the comparative biosensor 100 is in many respects configured similar to the biosensor 10. However, the neck portion 178 of the working electrode 122 has a width that is equal to or greater than the width of the body portion 176 (i.e., the width of the neck 178 is not reduced relative to the width of the main body 176). Additionally, the neck portion 178 of the working electrode 122 has a width that is substantially equal to the width of the neck portion 188 of the counter electrode 124.

As will become apparent below, compared to the biosensor 10, the particular configuration of the working electrode 122 of the comparative biosensor 100 is not specifically designed to minimize variations in the effective working electrode area $A_w$ as the position/placement of the inner boundary of the capillary chamber 118 is varied between the tolerance positions illustrated in FIGS. 8a-8c. Additionally, compared to the biosensor 10, the particular configuration of the working and counter electrodes 122, 124 of the comparative biosensor 100 are not specifically designed to As illustrated in Table B, in the exemplary embodiment of the biosensor 100, the variation of the effective working electrode area $A_w$ between the nominal and the maximum spacer positions is +4.89%, and the variation of the effective working electrode area $A_w$ between the nominal and the minimum spacer positions is −4.89%. Additionally, the overall variation of the effective working electrode area $A_w$ between the maximum and minimum spacer positions is −9.32%. In this exemplary embodiment, the width of the working electrode neck 178 is 0.100 mm, the width of the counter electrode neck 188 is 0.100 mm, the width of the working electrode main body 176 is 0.100 mm, and the width of the counter electrode main body 186 is 0.100 mm. Additionally, the nominal distance $d_{nom}$ is 1.000 mm, the maximum distance $d_{max}$ is 1.165 mm, and the minimum distance $d_{min}$ is 0.835 mm. As should be appreciated, due to the increased width of the working electrode neck 178 (relative to the reduced width of the working electrode neck 78), the comparative biosensor 100 exhibits greater variations in the effective working electrode area $A_w$ compared to the biosensor 10 as the position/placement of the inner boundary of the capillary chamber is varied due to tolerance levels associated with manufacturing of the biosensor. Accordingly, the comparative biosensor 100 does not exhibit the same improvements in precision and/or accuracy as exhibited by the biosensor 10.

Additionally, the comparative biosensor 100 likewise does not maintain as constant/uniform of a ratio R between the effective counter electrode area $A_c$ and the effective working electrode area $A_w$ compared to the biosensor 10 as the position/placement of the inner boundary of the capillary chamber is varied due to tolerance levels associated with manufacturing of the biosensor. Specifically, as illustrated in Table B, the variation in the area ratio R (i.e., $A_c/A_w$) between the nominal and the maximum spacer positions is −2.35%, and the variation in the area ratio R between the nominal and the minimum spacer positions is +2.55%. Additionally, the overall variation in the area ratio R between the maximum and minimum spacer positions is +5.02%. As should be appreciated, the comparative biosensor 100 exhibits greater variations in the area ratio R between the effective electrode areas $A_c$, $A_w$ compared to the biosensor 10 as the position/placement of the inner boundary of the capillary chamber is varied due to tolerance levels associated with manufacturing of the biosensor. Accordingly, it should be appreciated that the comparative biosensor 100 does not exhibit the same improvements in precision and/or accuracy as the biosensor 10.

Referring to Table C below in combination with FIGS. 9a-9c, shown therein is data associated with the comparative biosensor 200. As indicated above, the comparative biosensor 200 is in some respects configured similar to the biosensor 10. However, the neck portion 278 of the working electrode 222 has a width that is equal to or greater than the width of the body portion 276 (i.e., the width of the neck 278 is not reduced relative to the width of the main body 276). Additionally, the neck portion 278 of the working electrode 222 has a width that is substantially equal to the width of the first arm portion 286 of the counter electrode 224. Additionally, as indicated above, unlike the biosensor 10, the effective counter electrode portion of the counter electrode 224 does not include a single "neck" that extends across/intersects the inner boundary of the capillary chamber 218 at a single location (i.e., at the laterally-extending side wall 252c). Instead, the end of the first arm portion 286 and the entire length of the second arm portion 288 each extend across/intersect the inner boundary of the capillary chamber 218 at the laterally-extending side wall 252c.

As will become apparent below, compared to the biosensor 10, the particular configuration of the working electrode 222 and the counter electrode 224 of the comparative biosensor 200 are not specifically designed to minimize variations in the effective working electrode area $A_w$ and in the effective counter electrode area $A_c$ as the position/placement of the inner boundary of the capillary chamber 218 is varied between the tolerance positions illustrated in FIGS. 9a-9c. Additionally, compared to the biosensor 10, the particular configuration of the working and counter electrodes 222, 224 of the comparative biosensor 200 are not specifically designed to maintain a relatively constant/uniform ratio R between the effective counter electrode area $A_c$ and the effective working electrode area $A_w$ as the position/placement of the inner boundary of the capillary chamber 218 is varied between the tolerance positions illustrated in FIGS. 9a-9c.

electrode portion of the counter electrode 224 does not include a "neck" extending across/intersecting the inner boundary of the capillary chamber 218, as that term is typically referred to by those having ordinary skill in the art. Instead, the end of the first arm portion 286 and the entire length of the second arm portion 288 each extend across/intersect the inner boundary of the capillary chamber 218 at the laterally-extending side wall 252c.

As should also be appreciated, due to the increased width of the working electrode neck 278 (relative to the reduced width of the working electrode neck 78), the comparative biosensor 200 exhibits greater variations in the effective working electrode area $A_w$ compared to the biosensor 10 as the position/placement of the inner boundary of the capillary chamber is varied due to tolerance levels associated with manufacturing of the biosensor. Accordingly, the comparative biosensor 200 does not exhibit the same improvements in precision and/or accuracy as exhibited by the biosensor 10. As should be further appreciated, the comparative biosensor 200 likewise does not maintain as constant/uniform of a ratio R between the effective counter electrode area $A_c$ and the effective working electrode area $A_w$ compared to the biosensor 10 as the position/placement of the inner boundary of the capillary chamber is varied due to tolerance levels associated with manufacturing of the biosensor. Specifically, as illustrated in Table C, the variation in the area ratio R (i.e., $A_c/A_w$) between the nominal and the maximum spacer positions is +32.73, and the variation in the area ratio R between the nominal and the minimum spacer positions is −35.21%. Additionally, the overall variation in the area ratio R between the maximum and minimum spacer positions is −51.18%. As should be appreciated, the comparative biosensor 200 exhibits much greater variations in the area ratio R between the effective electrode areas $A_c$, $A_w$ compared to the biosensor 10 as the position/placement of the inner boundary of the capillary chamber is varied due to tolerance levels associated with manufacturing of the biosensor.

TABLE C

| | Effective Counter Electrode Area $A_C$ (mm²) | Effective Working Electrode Area $A_W$ (mm²) | % Variation of WE Area $A_W$ (from nominal) | Area Ratio R = $A_C/A_W$ | % Variation of Area Ratio R (from nominal) |
|---|---|---|---|---|---|
| Nominal Spacer Position ($d_{nom}$) | 1.08544 | 0.45493 | — | 2.386 | — |
| Maximum Spacer Position ($d_{max}$) | 1.49299 | 0.47143 | +3.63 | 3.167 | +32.73 |
| Minimum spacer Position ($d_{min}$) | 0.67789 | 0.43843 | −3.63 | 1.546 | −35.21 |

As illustrated in Table C, in the exemplary embodiment of the biosensor 200, the variation of the effective working electrode area $A_w$ between the nominal and the maximum spacer positions is +3.63%, and the variation of the effective working electrode area $A_w$ between the nominal and the minimum spacer positions is −3.63%. Additionally, the overall variation of the effective working electrode area $A_w$ between the maximum and minimum spacer positions is −7.00%. In this exemplary embodiment, the width of the working electrode neck 278 is 0.100 mm, the width of the working electrode main body 276 is 0.100 mm, the width of the counter electrode first arm portion 286 is 0.100 mm, and the width of the counter electrode second arm portion 288 is significantly greater than 0.100 mm. Additionally, the nominal distance $d_{nom}$ can be 1.000 mm, the maximum distance $d_{max}$ can be 1.165 mm, and the minimum distance $d_{min}$ can be 0.835 mm. As should be appreciated, the effective counter Accordingly, it should be appreciated that the comparative biosensor 200 does not exhibit the same improvements in precision and/or accuracy as the biosensor 10.

While the invention has been illustrated and described in detail in the drawings and foregoing description, the same is to be considered as illustrative and not restrictive in character, it being understood that only certain embodiments have been shown and described and that all changes and modifications that come within the spirit of the inventions are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A biosensor, comprising:
a capillary chamber having an inner boundary;
a working electrode including an effective working electrode portion positioned within the capillary chamber and comprising a main working electrode body portion and a working electrode neck extending from the main working electrode body portion, the main working electrode body portion having a generally linear configuration having an average width and the working electrode neck having a working electrode neck width that is reduced relative to the average width of the main working electrode body portion, the working electrode neck constituting the sole portion of the working electrode that extends across the inner boundary and out of the capillary chamber wherein the effective working electrode portion defines an effective working electrode area exposed to the capillary chamber including the entire area of the main working electrode body portion and an area of the working electrode neck contained within the capillary chamber; and
a counter electrode including an effective counter electrode portion positioned within the capillary chamber and comprising a main counter electrode body portion and a counter electrode neck extending from the main counter electrode body portion, the counter electrode neck having a counter electrode neck width, the counter electrode neck constituting the sole portion of the counter electrode that extends across the inner boundary and out of the capillary chamber wherein the effective counter electrode portion defines an effective counter electrode area exposed to the capillary chamber including the entire area of the main counter electrode body portion and an area of the counter electrode neck contained within the capillary chamber,
wherein the working electrode neck width is less than the counter electrode neck width, wherein the effective working electrode area is different than the effective counter electrode area,
wherein the working electrode neck extends across a single inner side wall of the inner boundary of the capillary chamber and the counter electrode neck extends across the same single inner side wall of the inner boundary of the capillary chamber, and
wherein a ratio between the effective working electrode area and the effective counter electrode area is independent of the relative position of the inner side wall along the reduced working electrode neck width.

2. The biosensor of claim 1, wherein the working electrode neck width is no more than one-half of the counter electrode neck width.

3. The biosensor of claim 1, wherein the working electrode neck width is no more than 80% of the average working electrode width.

4. The biosensor of claim 1, wherein the effective working electrode area is less than the effective counter electrode area.

5. The biosensor of claim 1,
wherein a first ratio between the effective working electrode area and the working electrode neck width is substantially equal to a second ratio between the effective counter electrode area and the counter electrode neck width.

6. The biosensor of claim 5, wherein the effective working electrode area is less than the effective counter electrode area.

7. The biosensor of claim 1, wherein the single inner side wall defining the inner boundary of the capillary chamber comprises a lateral side wall extending across a width of the biosensor.

8. The biosensor of claim 1, further comprising:
a support substrate including a first inner surface with the working and counter electrodes extending along the first inner surface; and
a spacer substrate including a first face and an opposite second face, the spacer substrate defining the inner boundary of the capillary chamber, the first face of the spacer substrate attached to the first inner surface of the support substrate.

9. The biosensor of claim 8, further comprising a cover substrate including a second inner surface attached to the second face of the spacer substrate; and
wherein the capillary chamber is defined by overlapping portions of the first inner surface of the support substrate and the second inner surface of the cover substrate in combination with the inner boundary defined by the spacer substrate.

10. The biosensor of claim 8, wherein the spacer substrate includes a channel extending therethrough from the first face to the second face, the channel defining the inner boundary of the capillary chamber.

11. The biosensor of claim 8, wherein the support substrate has a length dimension extending generally along a longitudinal axis and a width dimension extending generally along a transverse axis;
wherein the working electrode neck and the counter electrode neck each extend in a direction generally along the longitudinal axis.

12. The biosensor of claim 8, wherein the support substrate has a length dimension extending generally along a longitudinal axis and a width dimension extending generally along a transverse axis; and
wherein the working electrode neck and the counter electrode neck each extend across a single inner side wall defining the inner boundary of the capillary chamber, the single inner side wall extending generally along the transverse axis.

13. The biosensor of claim 12, wherein the effective working electrode portion includes a main body extending generally along the transverse axis and with the working electrode neck extending from the main body generally along the longitudinal axis.

14. The biosensor of claim 13, wherein the effective counter electrode portion includes a loop body extending peripherally about the main body of the effective working electrode portion and with the counter electrode neck extending from the loop body generally along the longitudinal axis.

15. A biosensor, comprising:
a capillary chamber having an inner boundary;
a working electrode including an effective working electrode portion positioned within the capillary chamber and comprising a main working electrode body portion with a working electrode neck extending therefrom, the working electrode neck having a reduced width relative to the main working electrode body portion and constituting the sole portion of the working electrode that extends across the inner boundary and out of the capillary chamber; and a counter electrode including an effective counter electrode portion positioned within the capillary chamber and comprising a main counter electrode body portion with a counter electrode neck extending therefrom, the main counter electrode body portion positioned generally adjacent the main working electrode body portion, the counter electrode neck constituting the sole portion of the counter electrode that extends across the inner boundary and out of the capillary chamber, wherein the effective working electrode portion defines an effective working electrode area exposed to the capillary chamber including the entire area of the main working electrode body portion and an area of the working electrode neck contained within the capillary chamber, wherein the effective counter electrode portion defines an effective counter electrode area exposed to the capillary chamber including the entire area of the main counter electrode body portion and an area of the counter electrode neck contained within the capillary chamber, wherein the effective working electrode area is different than the effective counter electrode area, wherein the reduced width of the working electrode neck is less than a width of the counter electrode neck width, wherein the working electrode neck extends across a single inner side wall of the inner boundary of the capillary chamber and the counter electrode neck extends across the same single inner side wall of the inner boundary of the capillary chamber, and wherein a ratio between the effective working electrode area and the effective counter electrode area is independent of the relative position of the inner side wall along the reduced width of the working electrode neck.

16. The biosensor of claim 15, wherein the main body of the effective counter electrode portion has a loop configuration extending peripherally about the main body of the effective working electrode portion.

17. The biosensor of claim 15, wherein the main body of the effective working electrode portion and the working electrode neck cooperate with one another to provide the effective working electrode portion with a T-shaped configuration.

18. The biosensor of claim 17, wherein the main body of the effective counter electrode portion has a C-shaped configuration extending peripherally about the T-shaped configuration of the effective working electrode portion.

19. The biosensor of claim 15,
wherein a first ratio between the effective working electrode area and a width of the working electrode neck is substantially equal to a second ratio between the effective counter electrode area and a width of the counter electrode neck.

20. The biosensor of claim 15, wherein the single inner side wall defining the inner boundary of the capillary chamber comprises a lateral side wall extending across a width of the biosensor.

21. The biosensor of claim 15, further comprising:
a support substrate including a first inner surface with the working and counter electrodes extending along the first inner surface, the support substrate having a length dimension extending generally along a longitudinal axis and a width dimension extending generally along a transverse axis; and a spacer substrate including a first face and an opposite second face, the spacer substrate including one or more inner side walls defining the inner boundary of the capillary chamber, the first face of the spacer substrate attached to the first inner surface of the support substrate; and wherein the working electrode neck and the counter electrode neck each extend generally along the longitudinal axis and across a single inner side wall defining the inner boundary of the capillary chamber, the single inner side wall extending generally along the transverse axis.

22. A biosensor, comprising:
a capillary chamber having an inner boundary;
a working electrode including an effective working electrode portion positioned within the capillary chamber and comprising a main working electrode body portion and a working electrode neck extending from the main working electrode body portion wherein the effective working electrode portion defines an effective working electrode area exposed to the capillary chamber including the entire area of the main working electrode body portion and an area of the working electrode neck contained within the capillary chamber, the working electrode neck having a reduced width relative to the main working electrode body portion and being the sole portion of the working electrode that extends out of the capillary chamber; and a counter electrode including an effective counter electrode portion positioned within the capillary chamber and comprising a main counter electrode body portion and a counter electrode neck extending from the main counter electrode body portion wherein the effective counter electrode portion defines an effective counter electrode area exposed to the capillary chamber including the entire area of the main counter electrode body portion and an area of the counter electrode neck contained within the capillary chamber, the counter electrode neck being the sole portion of the counter electrode that extends out of the capillary chamber, and wherein the working electrode neck extends across a single inner side wall of the inner boundary of the capillary chamber and the counter electrode neck extends across the same single inner side wall of the inner boundary of the capillary chamber, wherein the effective working electrode area is different than the effective counter electrode area, wherein the reduced width of the working electrode neck is less than a width of the counter electrode neck, and wherein a ratio between the effective working electrode area and the effective counter electrode area is independent of the relative position of the inner side wall along the reduced width of the working electrode neck.

23. The biosensor of claim 22, wherein the effective working electrode area is less than the effective counter electrode area.

24. The biosensor of claim 22,
wherein a first ratio between the effective working electrode area and the working electrode neck width is substantially equal to a second ratio between the effective counter electrode area and the counter electrode neck width.

25. The biosensor of claim 24, wherein the effective working electrode area is less than the effective counter electrode area.

* * * * *